(12) United States Patent
McComas et al.

(10) Patent No.: US 7,723,332 B2
(45) Date of Patent: May 25, 2010

(54) ARYL SULFONAMIDES USEFUL FOR MODULATION OF THE PROGESTERONE RECEPTOR

(75) Inventors: Casey Cameron McComas, Phoenixville, PA (US); Andrew Fensome, Wayne, PA (US); Michael Anthony Marella, Limerick, PA (US)

(73) Assignee: Wyeth LLC, Wilmington, DE (US)

( * ) Notice: Subject to any disclaimer, the term of this patent is extended or adjusted under 35 U.S.C. 154(b) by 0 days.

(21) Appl. No.: 12/041,716

(22) Filed: Mar. 4, 2008

(65) Prior Publication Data
US 2008/0221201 A1 Sep. 11, 2008

Related U.S. Application Data

(60) Provisional application No. 60/905,239, filed on Mar. 6, 2007.

(51) Int. Cl.
| | |
|---|---|
| A61K 31/5377 | (2006.01) |
| A61K 31/454 | (2006.01) |
| A61K 31/40 | (2006.01) |
| A61K 31/4025 | (2006.01) |
| C07D 413/02 | (2006.01) |
| C07D 401/02 | (2006.01) |
| C07D 207/30 | (2006.01) |
| C07D 207/48 | (2006.01) |

(52) U.S. Cl. ............ 514/235.5; 514/326; 514/422; 514/427; 544/141; 546/208; 548/518; 548/561

(58) Field of Classification Search ............ 514/426, 514/427, 422, 326, 235.5; 548/558, 561, 548/518; 546/208; 544/141
See application file for complete search history.

(56) References Cited

U.S. PATENT DOCUMENTS

| 7,291,643 | B2 | 11/2007 | McComas et al. |
| 7,297,713 | B2 | 11/2007 | McComas et al. |
| 2005/0159470 | A1 | 7/2005 | Bressi et al. |
| 2008/0064673 | A1 | 3/2008 | McComas et al. |

FOREIGN PATENT DOCUMENTS

| WO | WO-2004/058249 | 7/2004 |
| WO | WO-2004/082638 | 9/2004 |
| WO | WO-2006/023107 | 3/2006 |
| WO | WO 2006/063763 A1 * | 6/2006 |
| WO | WO-2007/016212 | 2/2007 |

OTHER PUBLICATIONS

Wolff et al., Burger's Medicinal Chemistry and Drug Discovery, 1994, Wiley-Interscience, Fifth Edition, vol. I: Principles and Practice, pp. 975-977.*
Kwon et al., Handbook of Essential Pharmacokinetics, Pharmacodynamics and Drug Metabolism for Industrial Scientists, 2001, http://www.myilibrary.com/Browse/open.asp?ID=4284&loc=1, Retrieved from the Internet Jun. 16, 2008, p. 213.*
Metabolomics [online], Retrieved from the Internet Jun. 16, 2008, URL: http://www.en.wikipedia.org/wiki/Metabolomics, p. 1.*
Collins, "Novel Pyrrole-Containing Progesterone Receptor Modulators", Bioorganic & Medicinal Chemistry Letters, vol. 14, (May 3, 2004), pp. 2185-2189.

* cited by examiner

*Primary Examiner*—Kamal A Saeed
*Assistant Examiner*—Kristin Bianchi
(74) *Attorney, Agent, or Firm*—Raquel M. Alvarez; Howson & Howson LLP

(57) ABSTRACT

In one embodiment, compounds of the following structure are described, wherein $R_1$ to $R_7$ are described herein.

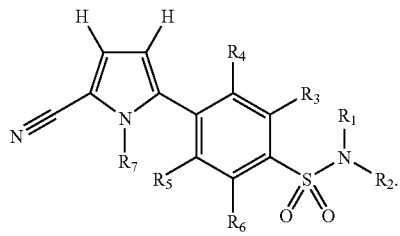

Also provided are methods for preparing these compounds and methods of contraception; treating or preventing fibroids; treating or preventing uterine leiomyomata; treating or preventing endometriosis, dysfunctional bleeding, and polycystic ovary syndrome; treating or preventing hormone-dependent carcinomas; providing hormone replacement therapy; stimulating food intake; synchronizing estrus; and treating cycle-related symptoms using the compounds described herein.

13 Claims, No Drawings

ARYL SULFONAMIDES USEFUL FOR MODULATION OF THE PROGESTERONE RECEPTOR

CROSS-REFERENCE TO RELATED APPLICATIONS

This application claims the benefit of the priority of U.S. Provisional Patent Application No. 60/905,239, filed Mar. 6, 2007.

BACKGROUND OF THE INVENTION

Progesterone receptor (PR) agonists and antagonists, also termed PR modulators, have been described for use in contraception and a variety of other indications.

What are needed are alternate non-steroidal compounds that are useful as PR modulators.

SUMMARY OF THE INVENTION

In one aspect, compounds of the following structure are described, wherein $R_1$-$R_7$ are defined herein.

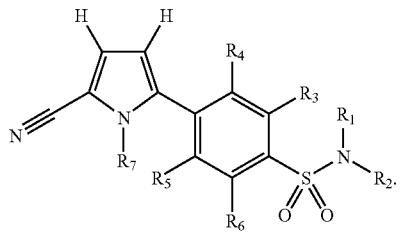

In a further aspect, methods of contraception; treating or preventing fibroids; treating or preventing uterine leiomyomata; treating or preventing endometriosis, dysfunctional bleeding, and polycystic ovary syndrome; treating or preventing hormone-dependent carcinomas; providing hormone replacement therapy; stimulating food intake; synchronizing estrus; and treating cycle-related symptoms using the compounds described herein are provided.

In another aspect, methods are described for preparing compounds the following structure, wherein $R_1$-$R_7$ are defined herein.

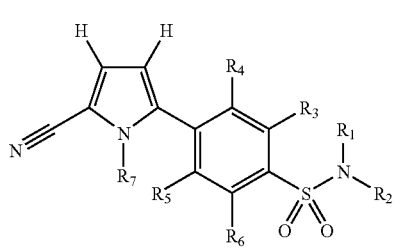

Other aspects and advantages of the invention will be readily apparent from the following detailed description of the invention.

DETAILED DESCRIPTION OF THE INVENTION

Compounds are provided which are progesterone receptor modulators. These compounds are those of formula I and have the structure:

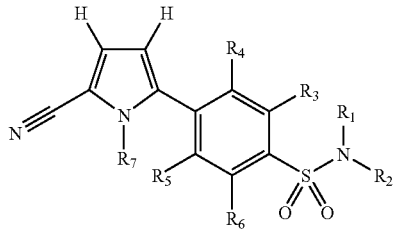

wherein, $R_1$ and $R_2$ are independently selected from among H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heteroaryl, substituted heteroaryl, heterocycle, substituted heterocycle, $C_3$ to $C_6$ alkenyl, $C_3$ to $C_6$ substituted alkenyl, $C_3$ to $C_6$ alkynyl, substituted $C_3$ to $C_6$ alkynyl, —$(CH_mX_n)_zCH_pX_q$, O—$C_1$ to $C_6$ alkyl, O—$C_1$ to $C_6$ substituted alkyl, and O—$(CH_mX_n)_zCH_pX_q$; or $R_1$ and $R_2$ may be taken together to form a ring of 4 to 8 ring atoms containing in its backbone carbon atoms and 1 to 4 N, O, S, or $SO_2$, and where any C-atom or N-atom of the ring is optionally substituted with $C_1$ to $C_4$ alkyl, F, or $CF_3$; $R_3$, $R_4$, $R_5$ and $R_6$ are independently selected from among H, halogen, CN, $C_1$ to $C_6$ alkyl, substituted $C_1$ to $C_6$ alkyl, —$(CH_mX_n)_zCH_pX_q$, $C_3$ to $C_6$ cycloalkyl, substituted $C_3$ to $C_6$ cycloalkyl, O—$C_1$ to $C_6$ alkyl, O—$C_1$ to $C_6$ substituted alkyl, OH, $NH_2$, NH—$(CH_mX_n)_zCH_pX_q$, O—$(CH_mX_n)_zCH_pX_q$, N—$\{(CH_mX_n)_zCH_pX_q\}_2$, aryl, substituted aryl, heteroaryl, substituted heteroaryl, heterocycle, and substituted heterocycle; X is halogen; m and n are, independently, 0 to 2, provided that m+n=2; p and q are, independently, 0 to 3, provided that p+q=3; z is 0 to 10; $R_7$ is selected from among H, $C_1$ to $C_6$ alkyl, substituted $C_1$ to $C_6$ alkyl, $C_3$ to $C_6$ cycloalkyl, and substituted $C_3$ to $C_6$ cycloalkyl; or a pharmaceutically acceptable salt, tautomer, metabolite or prodrug thereof.

In one embodiment, $R_7$ is a branched $C_1$ to $C_6$ alkyl. In another embodiment, $R_3$, $R_4$, $R_5$, and $R_6$ are H. In a further embodiment, $R_4$ is H or halogen. In still a further embodiment, $R_5$ is H or halogen. In another embodiment, $R_7$ is $CH_3$. In yet another embodiment, $R_7$ is $C_1$ to $C_6$ alkyl. In still a further embodiment, $R_1$ is H or $C_1$ to $C_6$ alkyl. In yet a further embodiment, $R_2$ is H, $C_1$ to $C_6$ alkyl, substituted $C_1$ to $C_6$ alkyl, $C_3$ to $C_6$ cycloalkyl, or $CF_3$. In another embodiment, $R_2$ is $CH_2$—$C_3$ to $C_8$ cycloalkyl. In yet another embodiment, $R_3$ or $R_6$ are NH—$(CH_mX_n)_zCH_pX_p$ such as $NH(C_1$ to $C_6$ alkyl). In a further embodiment, $R_3$ or $R_6$ are $N\{(CH_mX_n)_zCH_pX_q\}_2$ such as $N\{(C_1$ to $C_6$ alkyl$)\}_2$, wherein the $C_1$ to $C_6$ alkyl groups may be same or different. In still another embodiment, $R_1$ and $R_2$ are joined to form a pyrrolidine, piperidine, tetrahydropyran, morpholine, or pyrrole. In a further embodiment, $R_3$ or $R_6$ is H, halogen, $OCF_3$, $CF_3$, or $N(CH_3)_2$. In yet another embodiment, $R_4$ and $R_6$ are independently H or F. In a further embodiment, $R_3$ is H or $OCF_3$. In yet another embodiment, $R_4$ and $R_6$ are independently H or F. In another embodiment $R_4$ and $R_5$ are independently H or F. In still another embodiment, $R_5$ is H, $CF_3$, $N(CH_3)_2$, or F. In a further embodiment, $R_1$ is H or $C_1$ to $C_6$ alkyl; $R_2$ is H, $C_1$ to $C_6$ alkyl, substituted $C_1$ to $C_6$ alkyl, or $C_3$ to $C_6$ cycloalkyl; or $R_1$ and $R_2$ are joined with the N-atom to form a tetrahydropyrrole, piperidine, tetrahydropyran, morpholine, or pyrrole; $R_4$ and $R_5$ are independently H or F; $R_3$ and $R_6$ are independently H, halogen, $CF_3$, $OCF_3$, or $N(CH_3)_2$; or $R_7$ is $C_1$ to $C_6$ alkyl.

The inventors found that the compounds described herein not only functioned as effective PR modulators, but they have improved solubility as compared to other PR modulators in the art. Further, the compounds described herein have excellent bioavailability and are selective over other nuclear hormone receptors when administered in vivo.

The compounds as described can contain one or more asymmetric centers and can thus give rise to optical isomers and diastereomers. The compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups. In one embodiment, an alkyl group has 1 to about 8 carbon atoms (i.e., $C_1$, $C_2$, $C_3$, $C_4$, $C_5$ $C_6$, $C_7$, or $C_8$). In another embodiment, an alkyl group has 1 to about 6 carbon atoms (i.e., $C_1$, $C_2$, $C_3$, $C_4$, $C_5$ or $C_6$). In a further embodiment, an alkyl group has 1 to about 4 carbon atoms (i.e., $C_1$, $C_2$, $C_3$, or $C_4$).

The term "cycloalkyl" is used herein to refer to cyclic, saturated aliphatic hydrocarbon groups. In one embodiment, a cycloalkyl group has 3 to about 8 carbon atoms (i.e., $C_3$, $C_4$, $C_5$, $C_6$, $C_7$, or $C_8$). In another embodiment, a cycloalkyl group has 3 to about 6 carbon atoms (i.e., $C_3$, $C_4$, $C_5$ or $C_6$).

The term "alkenyl" is used herein to refer to both straight- and branched-chain alkyl groups having one or more carbon-carbon double bonds. In one embodiment, an alkenyl group contains 3 to about 8 carbon atoms (i.e., $C_3$, $C_4$, $C_5$, $C_6$, $C_7$, or $C_8$). In another embodiment, an alkenyl groups has 1 or 2 carbon-carbon double bonds and 3 to about 6 carbon atoms (i.e., $C_3$, $C_4$, $C_5$ or $C_6$).

The term "alkynyl" is used herein to refer to both straight- and branched-chain alkyl groups having one or more carbon-carbon triple bonds. In one embodiment, an alkynyl group has 3 to about 8 carbon atoms (i.e., $C_3$, $C_4$, $C_5$, $C_6$, $C_7$, or $C_8$). In another embodiment, an alkynyl group contains 1 or 2 carbon-carbon triple bonds and 3 to about 6 carbon atoms (i.e., $C_3$, $C_4$, $C_5$, or $C_6$).

The terms "substituted alkyl", "substituted alkenyl", "substituted alkynyl", and "substituted cycloalkyl" refer to alkyl, alkenyl, alkynyl, and cycloalkyl groups, respectively, having one, two, or more substituents independently selected from among, without limitation, hydrogen, halogen, CN, OH, $NO_2$, cycloalkyl, amino, aryl, heterocyclic, aryl, alkoxy, aryloxy, alkyloxy, alkylcarbonyl, alkylcarboxy, amino, and arylthio. In one embodiment, one or more of the carbon atoms in an alkyl has two or more substituents.

The term "arylthio" as used herein refers to the S(aryl) group, where the point of attachment is through the sulfur-atom and the aryl group can be substituted as noted above. The term "alkoxy" as used herein refers to the O(alkyl) group, where the point of attachment is through the oxygen-atom and the alkyl group can be substituted as noted above. The term "aryloxy" as used herein refers to the O(aryl) group, where the point of attachment is through the oxygen-atom and the aryl group can be substituted as noted above.

The term "alkylcarbonyl" as used herein refers to the C(O)(alkyl) group, where the point of attachment is through the carbon-atom of the carbonyl moiety and the alkyl group can be substituted as noted above.

The term "alkylcarboxy" as used herein refers to the C(O)O(alkyl) group, where the point of attachment is through the carbon-atom of the carboxy moiety and the alkyl group can be substituted as noted above.

The term "alkylamino" as used herein refers to both secondary and tertiary amines where the point of attachment is through the nitrogen-atom and the alkyl groups can be substituted as noted above. The alkyl groups can be the same or different.

The term "halogen" as used herein refers to Cl, Br, F, or I groups.

The term "aryl" as used herein refers to an aromatic, carbocyclic system, e.g., of about 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, $NO_2$, amino, alkyl, cycloalkyl, alkenyl, alkynyl, alkoxy, $C_1$ to $C_3$ perfluoroalkyl, $C_1$ to $C_3$ perfluoroalkoxy, aryloxy, alkyloxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl, which groups can be substituted. Desirably, a substituted aryl group is substituted with 1 to about 4 substituents.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents including halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, alkoxy, aryloxy, alkyloxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl, which groups may be optionally substituted. A substituted heterocycle or heteroaryl group may have 1, 2, 3, or 4 substituents.

The compounds may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

Pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, e.g., sodium, lithium, or potassium, and organic bases, such as ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts in the form of esters, and carbamates.

These salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The compounds discussed herein also encompass "metabolites" which are unique products formed by processing the compounds by the cell or subject. Desirably, metabolites are formed in vivo.

The compounds described herein may be prepared using reagents and steps that alone are known in the art. However, the combination of these reagents and steps by the inventors provide compounds of the following structure, wherein $R_1$-$R_7$ are defined above.

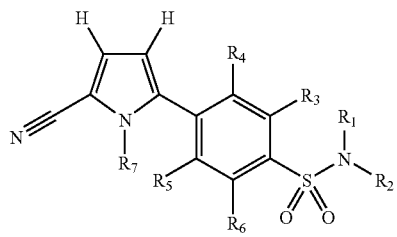

In summary, the compounds of formula I are prepared by combining an arylsulfonyl (1) with an amine (2) to form arylsulfonamide (3) under a variety of conditions. The arylsulfonamide may then be coupled with a cyanopyrrole to form the compounds of formula I. See, Scheme 1.

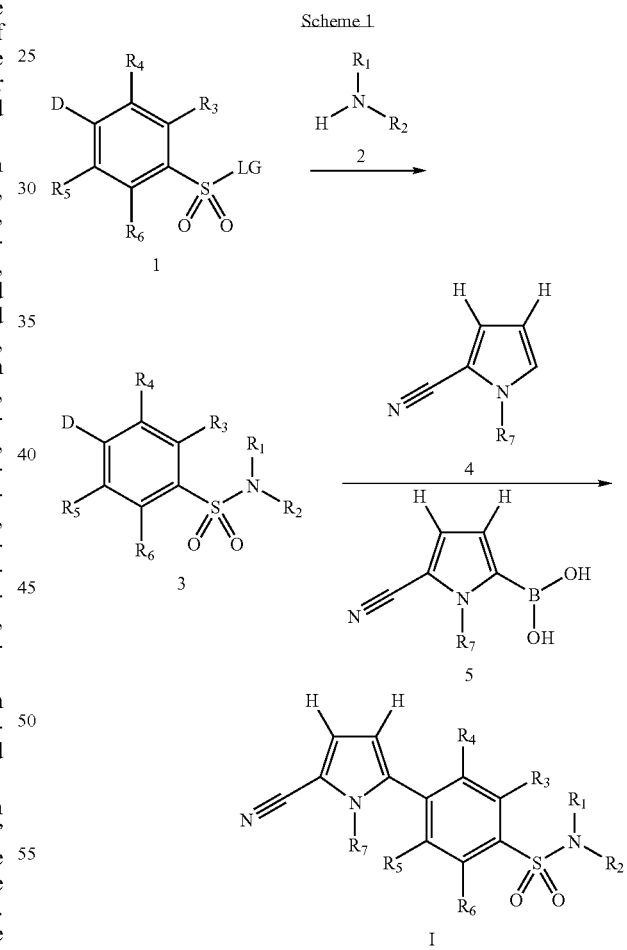

The first step includes reacting an amine, such as $HNR_1R_2$, and an arylsulfonyl of the following structure, wherein $R_3$-$R_6$ are defined above, LG is a leaving group which may be selected from among Cl, Br, F, or imidazole, and D is a halogen or sulfonate. In one embodiment, D is halogen. In a further embodiment, D is Br. In another example, D is sulfonate.

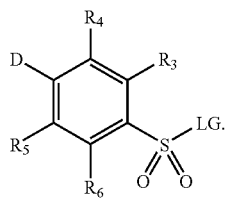

(1)

An amine, such as $HNR_1R_2$, where $R_1$ and $R_2$ are defined above, is utilized to prepare the sulfonamide. In one embodiment, greater than one equivalent of the amine is utilized. In another embodiment, about 10 equivalents of the amine are utilized. The reaction is also desirably performed in the presence of a base. A variety of bases may be selected for use in this reaction and may be selected by one of skill in the art. Examples of bases include sodium carbonate, potassium carbonate, cesium fluoride, potassium fluoride, or potassium phosphate, among others. The reaction is typically performed in methylene chloride, however other solvents may be selected by one of skill. By doing so, a sulfonamide of the following structure is prepared, wherein $R_1$-$R_6$ and D are defined above.

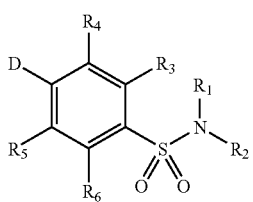

(3)

The sulfonamide is then coupled with a pyrrole comprising a leaving group. In one example, the pyrrole comprising a leaving group is a cyanopyrrole containining a leaving group. In a further example, the pyrrole comprising a leaving group is a boronic acid (5) of the following structure, wherein $R_7$ is defined above. In another example, the pyrrole comprising a leaving group is a tin derivative of boronic acid (5) of the following structure, wherein $R_7$ and "alkyl" are defined herein.

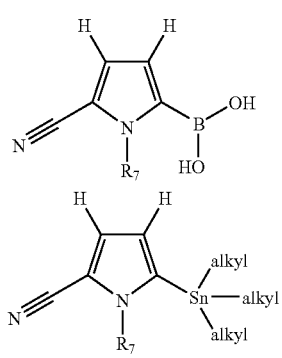

(5)

In a further example, the pyrrole comprising a leaving group may be prepared from lithium diisopropylamide, a trialkyl borate, and a pyrrole (4) of the following structure, wherein $R_7$ is defined above. A variety of trialkyl borates may be selected by one of skill in the art for use in the coupling.

Specific examples of trialkyl borates include, without limitation, trimethyl borate, triethyl borate, or triisopropyl borate.

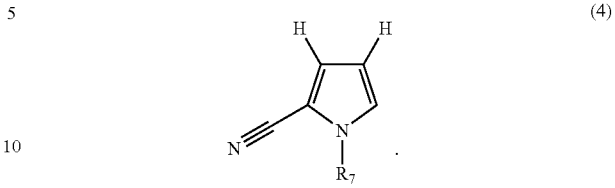

(4)

The coupling is desirably performed in the presence of a palladium catalyst. There are a variety of palladium catalysts available in the art that would be useful in the coupling and include, without limitation, tetrakis(triphenylphosphine) palladium (0) or palladium dibenzylidene acetone in the presence of tributylphosphine (Fu et al., J. Am. Chem. Soc., 2000, 122, 4020), as well as the catalysts/catalyst systems described in Hartwig et al. J. Org. Chem. 2002, 67, 5553. A base is also included for the coupling and may be selected by one of skill in the art. Bases that may be utilized include, without limitation, sodium carbonate, potassium carbonate, cesium fluoride, potassium fluoride, and potassium phosphate. Similarly, a variety of solvents may be selected for use in the coupling and include, without limitation, tetrahydrofuran (THF), dimethoxyethane (DME), dioxane, ethanol, water, toluene, or a combination thereof. Depending on the reactivity of the coupling partners and reagents, the reaction may be conducted up to the boiling point of the solvents, or may be accelerated under microwave irradiation, if necessary, which may readily be determined by one of skill in the art.

In one embodiment, the compounds of formula I are prepared as described in Scheme 2 by reacting bromoarylsulfonyl (1) with amine (2) to produce sulfonamide (3), which is then coupled with pyrrole boronic acid (5) or a pyrrole compound prepared using pyrrole (4).

Scheme 2

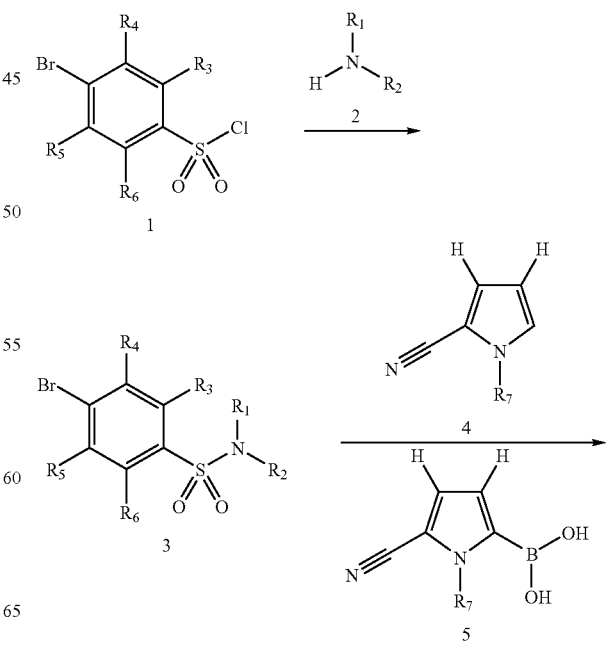

-continued

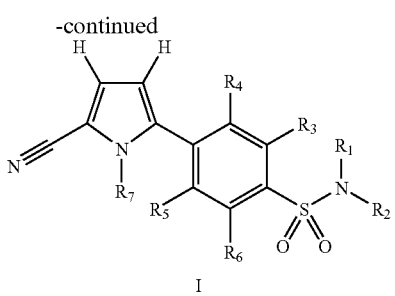

I

Also provided are pharmaceutical compositions containing one or more compounds described herein and a pharmaceutically acceptable carrier or excipient. In one embodiment, the methods of treatment include administering to a mammal a pharmaceutically effective amount of one or more compounds as described herein as progesterone receptor modulators.

The compounds may be combined with one or more pharmaceutically acceptable carriers or excipients, e.g., solvents, diluents and the like. Suitably, the compounds are formulated for delivery to a subject by any suitable route including, e.g., transdermal, mucosal (intranasal, buccal, vaginal), oral, parenteral, among others. A variety of suitable delivery devices can be utilized for these delivery routes and include, without limitation, tablets, caplets, capsules, gel tabs, dispersible powders, granules, suspensions, injectable solutions, transdermal patches, topical creams or gels, and vaginal rings, among others.

In preparing the compositions described herein, the compounds may be combined with one or more of a solid carrier, liquid carrier, adjuvant, suspending agent, syrup, and elixir, among others, the selection of which dependent on the nature of the active ingredient and the particular form of administration desired.

Solid carriers include, without limitation, starch, lactose, dicalcium phosphate, microcrystalline cellulose, sucrose and kaolin.

Liquid carriers include, without limitation, sterile water, dimethylsulfoxide (DMSO), polyethylene glycols, non-ionic surfactants and edible oils such as corn, peanut and sesame oils.

Adjuvants can include, without limitation, flavoring agents, coloring agents, preserving agents, and antioxidants, e.g., vitamin E, ascorbic acid, butylatedhydroxytoluene (BHT) and butylatedhydroxyanisole (BHA).

In one embodiment, the compound may be combined with a suspending agent, including about 0.05 to about 5% of suspending agent.

In another embodiment, the compound may be combined with a syrup containing, e.g., about 10 to about 50% of sugar.

In a further embodiment, the compound may be combined with an elixir containing, e.g., about 20 to about 50% ethanol, and the like.

When formulated for oral delivery, the compounds can be in the form of a tablet, capsule, caplet, gel tab, dispersible powder, granule, or suspension. One particularly desirable pharmaceutical composition, from the standpoint of ease of preparation and administration, are solid compositions, particularly tablets and hard-filled or liquid-filled capsules.

The compounds may also be administered parenterally or intraperitoneally as solutions, suspensions, dispersions, or the like. Such pharmaceutical preparations may contain, e.g., about 25 to about 90% of the compound in combination with the carrier. Desirably, the pharmaceutical preparation contains about 5% and 60% by weight of the compound. In one embodiment, the compounds are administered in solutions or suspensions, whereby the compounds are present as free bases or pharmacologically acceptable salts and are prepared in water suitably mixed with a surfactant such as hydroxypropylcellulose. In another embodiment, the solutions or suspensions containing the compound may contain about 0.05 to about 5% of a suspending agent in an isotonic medium. In a further embodiment, the compounds are administered in dispersions, which may be prepared in glycerol, liquid, polyethylene glycols and mixtures thereof in oils.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier utilized in the injectable form may be a solvent or dispersion medium containing, e.g., water, ethanol (e.g., glycerol, propylene glycol and liquid polyethylene glycol), suitable mixtures thereof, and vegetable oil.

The compounds may also be administered via a vaginal ring. Suitably, use of the vaginal ring is timed to cycle to which the compound is being administered, including a 28-day cycle. However, the vaginal ring can be inserted for longer or shorter periods of time. See, U.S. Pat. Nos. 5,972,372; 6,126,958; and 6,125,850, which are hereby incorporated by reference, for formulations of the vaginal ring that can be used.

The compounds can also be delivered via a transdermal patch. Suitably, use of the patch is timed to the length of the cycle, including a 28 day cycle. However, the patch can remain in place for longer or shorter periods of time.

The compounds may be utilized in methods of contraception, hormone replacement therapy, and the treatment and/or prevention of benign and malignant neoplastic disease; cycle-related symptoms; fibroids, including uterine fibroids; leiomyomata; polycystic ovary syndrome; endometriosis; benign prostatic hypertrophy; carcinomas and adenocarcinomas of the endometrium, ovary, breast, colon, prostate, pituitary, meningioma and other hormone-dependent tumors; dysmenorrhea; dysfunctional uterine bleeding; symptoms of premenstrual syndrome and premenstrual dysphoric disorder; and for inducing amenorrhea. Additional uses of the present progesterone receptor modulators include stimulating food intake and the synchronization of estrus in livestock. In one embodiment, the neoplastic disease is hormone-dependent.

The term "cycle-related symptoms" refers to psychological symptoms (e.g., mood change, irritability, anxiety, lack of concentration, or decrease in sexual desire) and physical symptoms (e.g., dysmenorrhea, breast tenderness, bloating, fatigue, or food cravings) associated with a woman's menstrual cycle. Cycle-related symptoms include, but are not limited to, dysmenorrhea and moderate to severe cycle-related symptoms.

When utilized for these purposes, the compounds can be administered in combination with other agents, as well as in combination with each other. Such agents include, without limitation, progestins, antiprogestins, estrogens, antiestrogens, selective estrogen receptor modulators (SERMS), among others. Progestins can include, without limitation, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Estrogens can include, without limitation, ethinyl estradiol. The compounds described herein can be combined with one or more of these agents, delivered concurrently therewith one or more of these agents, delivered prior to one or more of these agents, or delivered subsequent to one or more of these agents.

A patient or subject being treated is a mammalian subject and typically a female. Desirably, the subject is a human. However, as used herein, a female can include non-human mammals, e.g., cattle or livestock, horses, pigs, domestic animals, etc.

The effective dosage of the compound may vary depending on the particular compound employed, the mode of administration and the severity of the condition being treated. However, in general, satisfactory results are obtained when the compounds are administered at a daily dosage of about 0.5 to about 500 mg/kg of animal body weight, about 1 to about 400 mg/kg, about 5 to about 300 mg/kg, about 10 to about 250 mg/kg, about 50 to about 200 mg/kg, or about 100 to 150 mg/kg. For most large mammals, the total daily dosage is from about 1 to 100 mg. In one embodiment, the total daily dosage is from about 2 to 80 mg. This dosage regimen may be adjusted to provide the optimal therapeutic response. For example, several divided doses may be administered daily or the dose may be proportionally reduced as indicated by the exigencies of the therapeutic situation.

As previously noted, the compounds may be administered via a vaginal ring. In one embodiment, the ring is inserted into the vagina and it remains in place for 3 weeks. During the fourth week, the vaginal ring is removed and menses occurs. The following week, a new ring is inserted to be worn another 3 weeks until it is time for the next period. In another embodiment, the vaginal ring is inserted weekly and is replaced for 3 consecutive weeks. Then, following 1 week without the ring, a new ring is inserted to begin a new regimen. In yet another embodiment, the vaginal ring is inserted for longer or shorter periods of time.

Further, the previously mentioned transdermal patch is applied via a suitable adhesive on the skin, where it remains in place for at least one week. In one embodiment, the transdermal patch remains in place for one week and is replaced weekly for a total of 3 weeks. In another embodiment, the transdermal patch remains in place for two weeks. In a further embodiment, the transdermal patch remains in place for three weeks. During the fourth week, no patch is applied and menses occurs. The following week, a new patch is applied to be worn to begin a new regimen. In yet another embodiment, the patch remains in place for longer or shorter periods of time.

When used for contraception, the method typically includes delivering a daily dosage unit containing a compound for 28 consecutive days to a female of child-bearing age. Desirably, the method includes delivering the compound over a period of 21 to 27 consecutive days followed by 1 to 7 consecutive days in which no effective amount or no amount of the compound is delivered. Optionally, the period of 1 to 7 days in which no effective amount of the compound is delivered to the subject can involve delivery of a second phase of daily dosage units of 1 to 7 days of a pharmaceutically acceptable placebo. Alternatively, during this "placebo period", no placebo is administered. The compound may optionally be administered in combination with a progestin, antiprogestin, estrogen, or combination thereof.

In another embodiment, the method includes delivering a compound for 21 consecutive days, followed by 7 days in which no effective amount of the compound is delivered. Optionally, during these 7 days, a second phase of 7 daily dosage units of an orally and pharmaceutically acceptable placebo can be delivered. The compound may optionally be administered in combination with a progestin, antiprogestin, estrogen, anti-estrogen, SERM or combination thereof.

In a further embodiment, the method includes delivering a compound for 23 consecutive days, followed by 5 days in which no effective amount of the compound is delivered. Optionally, during these 5 days, a second phase of 5 daily dosage units of an orally and pharmaceutically acceptable placebo can be delivered. The compound may optionally be administered in combination with a progestin, antiprogestin, estrogen, anti-estrogen, SERM or combination thereof.

In yet another embodiment, the method includes delivering a compound for 25 consecutive days, followed by 3 days in which no effective amount of the compound is delivered. Optionally, during these 3 days, a second phase of 3 daily dosage units of an orally and pharmaceutically acceptable placebo can be delivered. The compound may optionally be administered in combination with a progestin, antiprogestin, estrogen, anti-estrogen, SERM, or combination thereof.

In still a further embodiment, the method includes delivering a compound for 27 consecutive days, followed by 1 day in which no effective amount of the compound is delivered. Optionally, a second phase of 1 daily dosage unit of an orally and pharmaceutically acceptable placebo can be delivered. The compound may optionally be administered in combination with a progestin, antiprogestin, estrogen, anti-estrogen, SERM, or combination thereof.

In another embodiment, a method of contraception includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In yet a further embodiment, a method of contraception includes administering to a female of child bearing age for 28 consecutive days: (a) a first phase of from 14 to 24 daily dosage units of a compound described herein; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

In yet a further embodiment, a method of contraception is provided and includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In another embodiment, a method of contraception is provided and includes administering to a female of child bearing age for 28 consecutive days: (a) a first phase of from 14 to 24 daily dosage units of a compound described herein; (b) a second phase of from 1 to 11 daily dosage units of an anti-progestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

Also provided are kits or packages of pharmaceutical formulations designed for use in the regimens described herein. Suitably, the kits contain one or more compounds as described herein.

Advantageously, for use in the kits, the compound is formulated for the desired delivery vehicle and route. For example, the compound can be formulated for oral delivery, parenteral delivery, vaginal ring, transdermal delivery, or mucosal delivery, as discussed in detail above. The kit is preferably a pack (e.g. a blister pack) containing daily doses arranged in the order in which they are to be taken.

In each of the regimens and kits described herein, it is preferred that the daily dosage of each pharmaceutically active component of the regimen remain fixed in each particular phase in which it is administered. It is also understood that the daily dose units described are to be administered in the order described, with the first phase followed in order by the optional phases, including any second and third phases. To help facilitate compliance with each regimen, it is also preferred that the kits contain the placebo described for the final days of the cycle. It is further preferred that each package or kit contain a pharmaceutically acceptable package having indicators for each day of the 28-day cycle, such as a labeled blister package, dial dispenser, or other packages known in the art.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

In one embodiment, the kit is designed for daily oral administration over a 28-day cycle, desirably for one oral administration per day, and organized so as to indicate a single oral formulation or combination of oral formulations to be taken on each day of the 28-day cycle. Desirably each kit will include oral tablets to be taken on each the days specified; desirably one oral tablet will contain each of the combined daily dosages indicated. For example, a kit can contain 21 to 27 daily dosage units of an effective amount of the compound, optionally, 1 to 7 daily dosage units of a placebo and other appropriate components including, e.g., instructions for use.

In another embodiment, the kit is designed for weekly or monthly administration via a vaginal ring over a 28-day cycle. Suitably, such a kit contains individual packaging for each of the vaginal rings, i.e. one to three, required for a monthly cycle and other appropriate components, including, e.g., instructions for use.

In a further embodiment, the kit is designed for weekly or monthly administration via a transdermal patch over a 28-day cycle. Suitably, such a kit contains individual packaging for each of the patches, i.e. one to three, required for a monthly cycle and other appropriate components, including, e.g., instructions for use.

In still another embodiment, the kit is designed for parenteral delivery of the compound. Such a kit is typically designed for delivery at home and may include needles, syringes, and other appropriate packaging and instructions for use.

In yet another embodiment, the kit contains the compound in a gel or cream formulation. Optionally, the kit can include appropriate packaging such as a tube or other container, an applicator, and/or instructions for use.

In a further embodiment, the kit includes (a) a first phase of from 14 to 21 daily dosage units of a progestational agent equal in progestational activity to about 35 to about 150 µg levonorgestrel; (b) a second phase of from 1 to 11 daily dosage units of a compound described herein; and (c) a third phase of daily dosage units of an orally and pharmaceutically acceptable placebo; wherein the total number of the daily dosage units in the first phase, second phase and third phase equals 28.

In still another embodiment, a kit contains (a) a first phase of from 14 to 21 daily dosage units of a compound described herein; (b) a second phase of from 1 to 11 daily dosage units of an antiprogestin compound; and (c) a third phase of daily dosage units of an orally and pharmaceutically acceptable placebo; wherein the total number of the daily dosage units in the first phase, second phase and third phase equals 28.

The following examples are illustrative only and are not intended to be a limitation on the present invention.

EXAMPLES

Example 1

Preparation of 4-(5-cyano-1-methyl-1H-pyrrol-2-yl)-N-methylbenzenesulfonamide

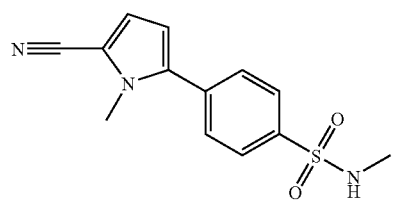

Step 1: Preparation of
4-bromo-N-methylbenzenesulfonamide

General Procedure A for Preparation of Sulfonamides from Sulfonyl Chlorides

4-Bromobenzene sulfonyl chloride (0.40 g, 1.56 mmol) and methylamine (10 mL, 33% in ethanol) were stirred in a sealed tube for 16 hours. The reaction mixture was concentrated in vacuo onto the Celite® reagent. The crude product was purified via Isco chromatography (the Redisep™ column, silica, gradient 0-3% ethyl acetate-dichloromethane) to provide 4-bromo-N-methylbenzenesulfonamide (0.11 g, 28%). MS (ESI) m/z 250. High performance liquid chromatography (HPLC) purity 100.0% at 210-370 nm, 7.4 min.; the Xterra® RP18 column, 3.5µ, 150×4.6 mm column, 1.2 mL/min., 85/15-5/95 (ammonium formate buffer pH=3.5/Acetonitrile (ACN)+MeOH) for 10 min., hold 4 min.

General Procedure B for Coupling of Aryl Bromides and Boronic Acids

Step 2

4-Bromo-N-methylbenzenesulfonamide (100 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 µL, 0.02 mmol, 10 wt % in hexane) was added and the reaction was stirred for 16 hours. The reaction mixture was filtered through silica and rinsed with ethyl acetate. The solvent was concentrated in vacuo to provide the crude product. The crude product was pre-adsorbed onto the Celite® reagent and purified via Isco chromatography (the Redisep™ column, silica, gradient 5-50% ethyl acetate in hexane) to afford 4-(5-cyano-1-methyl-1H-pyrrol-2-yl)-N-methylbenzenesulfonamide (28 mg, 25%). MS (ESI) m/z 275. HPLC purity 100.0% at 210-370 nm, 9.0 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 2

Preparation of 4-(5-cyano-1-methyl-1H-pyrrol-2-yl)-N,N-dimethylbenzenesulfonamide

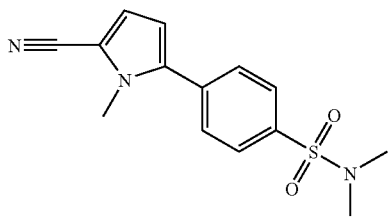

Step 1: In an analogous manner to General Procedure A, 4-Bromobenzene sulfonyl chloride (0.40 g, 1.56 mmol) and dimethylamine (10 mL, 33% in ethanol) were stirred together for 16 hours. 4-bromo-N,N-dimethylbenzenesulfonamide (0.11 g) was provided after purification. MS (ESI) m/z 264. HPLC purity 100.0% at 210-370 mn, 8.3 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: In an analogous manner to General Procedure B, 4-bromo-N,N-dimethylbenzenesulfonamide (105 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 µL, 0.02 mmol, 10 wt % in hexane) was added and the reaction was stirred for 16 hours. 4-(5-cyano-1-methyl-1H-pyrrol-2-yl)-N,N-dimethylbenzenesulfonamide (30 mg, 26%) was provided after purification. HRMS: calcd for $C_{14}H_{15}N_3O_2S$+H$^+$, 290.09577; found (ESI, [M+H]$^+$), 290.0964. HPLC purity 100.0% at 210-370 nm, 9.8 min.; the Xterra® RP18 column, 3.5µ column, 150×4.6 mm column, 1.2 mL/min., 85/15-5/95 (ammonium formate buffer pH=3.5/ACN+MeOH) for 10 min., hold 4 min.

Example 3

Preparation of 4-(5-cyano-1-methyl-1H-pyrrol-2-yl)-N-ethylbenzenesulfonamide

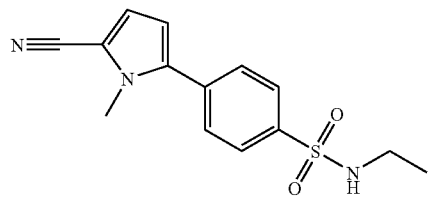

Step 1: Following general procedure A, 4-Bromobenzene sulfonyl chloride (0.40 g, 1.56 mmol) and ethylamine (5 mL, [2.0M], 10 mmol) were stirred together for 16 hours. 4-bromo-N-ethylbenzenesulfonamide (0.11 g) was provided after purification. MS (ESI) m/z 264. HPLC purity 100.0% at 210-370 nm, 8.1 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: In an analogous manner to general procedure B, 4-bromo-N-ethylbenzenesulfonamide (105 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 µL, 0.02 mmol, 10 wt % in hexane) was added and the reaction was stirred for 16 hours. 4-(5-cyano-1-methyl-1H-pyrrol-2-yl)-N-ethylbenzenesulfonamide (15 mg, 13%) was provided after purification. MS (ESI) m/z 289. HPLC purity 100.0% at 210-370 nm, 9.6 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 4

Preparation of 4-(5-cyano-1-methyl-1H-pyrrol-2-yl)-N-propylbenzenesulfonamide

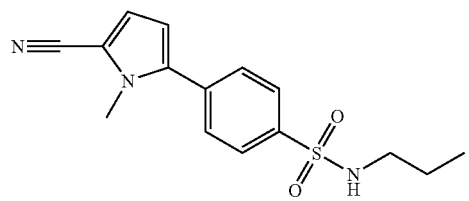

Step 1: General Procedure C for formation of sulfonamides from sulfonyl chlorides 4-Bromobenzene sulfonyl chloride (0.40 g, 1.5mmol) and propylamine (0.32 mL, 3.90 mmol) were dissolved in dry dichloromethane (5 mL) in a sealed tube. The mixture was stirred for 16 hours then concentrated in vacuo onto the Celite® reagent. The crude product was purified via Isco chromatography (the Redisep™ column, silica, gradient 0-3% ethyl acetate-dichloromethane) to provide 4-bromo-N-propylbenzenesulfonamide (0.12 g, 28%). MS (ESI) m/z 278. HPLC purity 100.0% at 210-370 nm, 8.8 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-propylbenzenesulfonamide (111 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 4-(5-cyano-1-methyl-1H-pyrrol-2-yl)-N-propylbenzenesulfonamide (21 mg, 17%) was provided after purification. MS (ESI) m/z 303. HPLC purity 100.0% at 210-370 mn, 10.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 5

Preparation of 4-(5-cyano-1-methyl-1H-pyrrol-2-yl)-N-isopropylbenzenesulfonamide

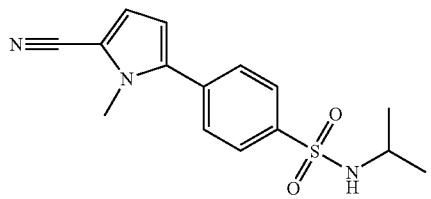

Step 1: According to general procedure C, 4-Bromobenzene sulfonyl chloride (0.40 g, 1.56 mmol) and isopropylamine (0.33 mL, 3.90 mmol) were stirred together with dry dichloromethane (5 mL) for 16 hours. 4-bromo-N-isopropylbenzenesulfonamide (0.12 g, 28%) was provided after purification. MS (ESI) m/z 278. HPLC purity 100.0% at 210-370 nm, 8.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-isopropylbenzenesulfonamide (111 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 4-(5-cyano-1-methyl-1H-pyrrol-2-yl)-N-isopropylbenzenesulfonamide (15 mg, 12%) was provided after purification. MS (ESI) m/z 303. HPLC purity 100.0% at 210-370 nm, 10.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 6

Preparation of 4-(5-cyano-1-methyl-1H-pyrrol-2-yl)-N-isobutylbenzenesulfonamide

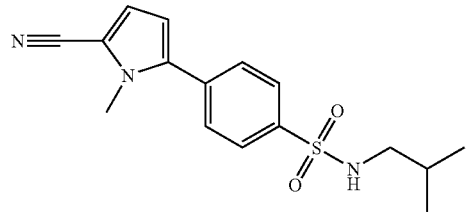

Step 1: According to general procedure C, 4-Bromobenzene sulfonyl chloride (0.40 g, 1.56 mmol) and isobutylamine (0.39 mL, 3.90 mmol) were stirred together with dry dichloromethane (5 mL) for 16 hours. 4-bromo-N-isobutylbenzenesulfonamide (0.12 g, 28%) was provided after purification. MS (ESI) m/z 292. HPLC purity 100.0% at 210-370 nm, 9.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-isobutylbenzenesulfonamide (117 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 4-(5-cyano-1-methyl-1H-pyrrol-2-yl)-N-isobutylbenzenesulfonamide (11 mg, 9%) was provided after purification. MS (ESI) m/z 317. HPLC purity 100.0% at 210-370 nm, 10.8 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 7

Preparation of 4-(5-cyano-1-methyl-1H-pyrrol-2-yl)-N-ethyl-N-methylbenzenesulfonamide

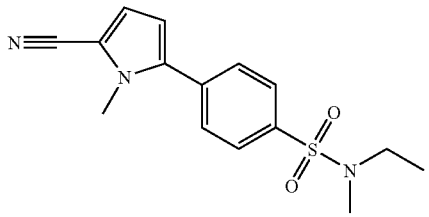

Step 1: According to general procedure C, 4-Bromobenzene sulfonyl chloride (0.40 g, 1.56 mmol) and N-Ethyl-N-methylamine (0.33 mL, 3.90 mmol) were stirred together in dry dichloromethane (5 mL) for 16 hours. 4-bromo-N-ethyl- N-methylbenzenesulfonamide (0.12 g, 28%) was provided after purification. MS (ESI) m/z 278. HPLC purity 99.2% at 210-370 nm, 8.9 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 mm.

Step 2: According to general procedure B, 4-bromo-N-ethyl-N-methylbenzenesulfonamide (111 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 4-(5-cyano-1-methyl-1H-pyrrol-2-yl)-N-ethyl-N-methylbenzenesulfonamide (17 mg, 14%) was provided after purification. MS (ESI) m/z 303. HPLC purity 99.5% at 210-370 nm, 10.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 8

Preparation of 4-(5-cyano-1-methyl-1H-pyrrol-2-yl)-N,N-diethylbenzenesulfonamide

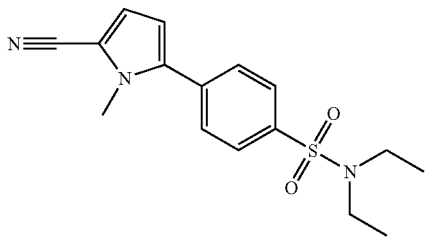

Step 1: According to general procedure C, 4-Bromobenzene sulfonyl chloride (0.40 g, 1.56 mmol) and diethylamine (0.40 mL, 3.90 mmol) were stirred together in dry dichloromethane (5 mL) for 16 hours. 4-bromo-N,N-diethylbenzenesulfonamide (0.12 g) was provided after purification. MS (ESI) m/z 293. HPLC purity 99.2% at 210-370 nm, 9.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N,N-diethylbenzenesulfonamide (117 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 4-(5-cyano-1-methyl-1H-pyrrol-2-yl)-N,N-diethylbenzenesulfonamide (27 mg, 21%) was provided after purification. MS (ESI) m/z 317. HPLC purity 100.0% at 210-370 nm, 10.8 min.; the Xterr® RP18 column, 3.5μ, 150×4.6 mm column, 1.2 mL/min., 85/15-5/95 (ammonium formate buffer pH=3.5/ACN+MeOH) for 10 min., hold 4 min.

Example 9

Preparation of N-(tert-butyl)-4-(5-cyano-1-methyl-1H-pyrrol-2-yl)benzenesulfonamide

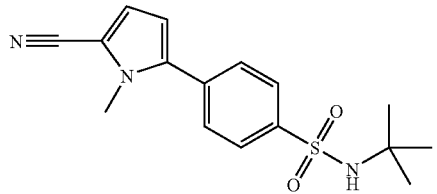

Step 1: According to general procedure C, 4-Bromobenzene sulfonyl chloride (0.40 g, 1.56 mmol) and tert-butylamine (0.41 mL, 3.90 mmol) were stirred together in dry dichloromethane (5 mL) for 16 hours. 4-bromo-N-(tert-butyl)benzenesulfonamide (0.12 g) was provided after purification. MS (ESI) m/z 292. HPLC purity 100.0% at 210-370 nm, 9.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-(tert-butyl)benzenesulfonamide (117 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. N-(tert-butyl)-4-(5-cyano-1-methyl-1H-pyrrol-2-yl)benzenesulfonamide (19 mg, 15%) was provided after purification. MS (ESI) m/z 317. HPLC purity 100.0% at 210-370 nm, 10.5 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 10

Preparation of 1-methyl-5-[4-(pyrrolidin-1-ylsulfonyl)phenyl]-1H-pyrrole-2-carbonitrile

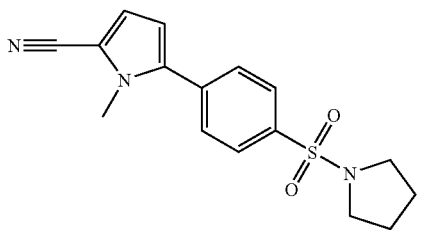

Step 1: According to general procedure C, 4-Bromobenzene sulfonyl chloride (0.40 g, 1.56 mmol) and pyrrolidine (0.32 mL, 3.90 mmol) were stirred together in dry dichloromethane (5 mL) for 16 hours. 1-[(4-bromophenyl)sulfonyl]pyrrolidine (0.12 g) was provided after purification. HRMS:

calcd for $C_{10}H_{12}BrNO_2S+H^+$, 289.98449; found (ESI, [M+H]$^+$), 289.9847. HPLC purity 99.1% at 210-370 nm, 8.9 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 1-[(4-bromophenyl)sulfonyl]pyrrolidine (116 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 1-methyl-5-[4-(pyrrolidin-1-ylsulfonyl)phenyl]-1H-pyrrole-2-carbonitrile (7 mg, 6%) was provided after purification. HRMS: calcd for $C_{16}H_{17}N_3O_2S+H^+$, 316.11142; found (ESI, [M+H]$^+$), 316.1114. HPLC purity 100.0% at 210-370 nm, 10.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 11

Preparation of 1-methyl-5-[4-(piperidin-1-ylsulfonyl)phenyl]-1H-pyrrole-2-carbonitrile

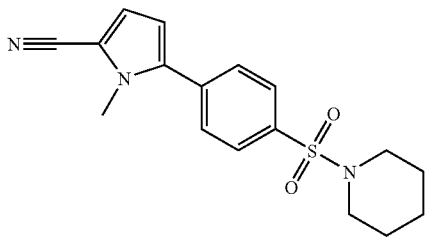

Step 1: According to general procedure C, 4-Bromobenzene sulfonyl chloride (0.40 g, 1.56 mmol) and piperidine (0.38 mL, 3.90 mmol) were stirred together in dry dichloromethane (5 mL) for 16 hours. 1-[(4-bromophenyl)sulfonyl]piperidine (0.13 g) was provided after purification. HRMS: calcd for $C_{11}H_{14}BrNO_2S+H^+$, 304.00014; found (ESI, [M+H]$^+$), 304.0009. HPLC purity 99.2% at 210-370 nm, 9.8 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 1-[(4-bromophenyl)sulfonyl]piperidine (121 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 1-methyl-5-[4-(piperidin-1-ylsulfonyl)phenyl]-1H-pyrrole-2-carbonitrile (11 mg, 8%) was provided after purification. MS (ESI) m/z 329. HPLC purity 100.0% at 210-370 nm, 11.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 12

Preparation of 1-methyl-5-[4-(morpholin-4-ylsulfonyl)phenyl]-1H-pyrrole-2-carbonitrile

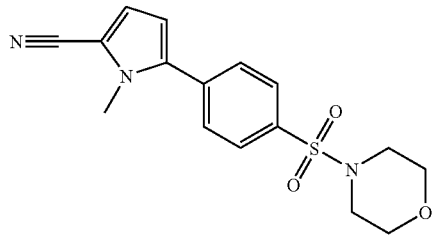

Step 1: According to general procedure C, 4-Bromobenzene sulfonyl chloride (0.40 g, 1.56 mmol) and morpholine (0.34 mL, 3.90 mmol) were stirred together in dry dichloromethane (5 mL) for 16 hours. 4-[(4-bromophenyl)sulfonyl]morpholine (0.13 g, 28%) was provided after purification. MS (ESI) m/z 306. HPLC purity 100.0% at 210-370 nm, 8.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-[(4-bromophenyl)sulfonyl]morpholine (122 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 1-methyl-5-[4-(morpholin-4-ylsulfonyl)phenyl]-1H-pyrrole-2-carbonitrile (11 mg, 8%) was provided after purification. MS (ESI) m/z 331. HPLC purity 100.0% at 210-370 nm, 9.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 13

Preparation of 4-(5-cyano-1-methyl-1H-pyrrol-2-yl)-N-cyclobutylbenzenesulfonamide

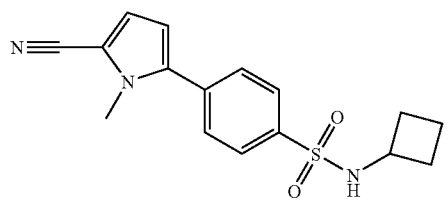

Step 1: According to general procedure C, 4-Bromobenzene sulfonyl chloride (0.40 g, 1.56 mmol) and cyclobutylamine (0.33 mL, 3.90 mmol) were stirred together in dry dichloromethane (5 mL) for 16 hours. 4-bromo-N-cyclobutylbenzenesulfonamide (0.13 g) was provided after purification. MS (ESI) m/z 290. HPLC purity 95.6% at 210-370 nm, 9.1 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclobutylbenzenesulfonamide (117 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 µL, 0.02 mmol, 10 wt % in hexane) was added and the reaction was stirred for 16 hours. 4-(5-cyano-1-methyl-1H-pyrrol-2-yl)-N-cyclobutylbenzenesulfonamide (20 mg, 16%) was provided after purification. MS (ESI) m/z 315. HPLC purity 98.8% at 210-370 nm, 10.4 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 14

Preparation of 4-(5-cyano-1-methyl-1H-pyrrol-2-yl)-N-cyclopropylbenzenesulfonamide

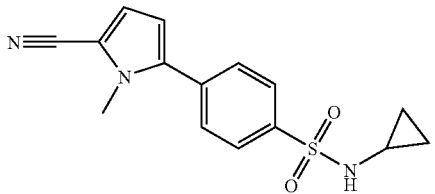

Step 1: According to general procedure C, 4-Bromobenzene sulfonyl chloride (0.40 g, 1.56 mmol) and cyclopropylamine (0.27 mL, 3.90 mmol) were stirred together in dry dichloromethane (5 mL) for 16 hours. 4-bromo-N-cyclopropylbenzenesulfonamide (0.12 g) was provided after purification. MS (ESI) m/z 276. HPLC purity 100.0% at 210-370 nm, 8.4 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclopropylbenzenesulfonamide (110 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 µL, 0.02 mmol, 10 wt % in hexane) was added and the reaction was stirred for 16 hours. 4-(5-cyano-1-methyl-1H-pyrrol-2-yl)-N-cyclopropylbenzenesulfonamide (34 mg, 28%) was provided after purification. MS (ESI) m/z 301. HPLC purity 100.0% at 210-370 nm, 9.6 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 15

Preparation of 4-(5-cyano-1-methyl-1H-pyrrol-2-yl)-N-cyclohexylbenzenesulfonamide

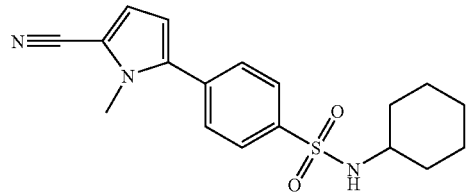

Step 1: According to general procedure C, 4-Bromobenzene sulfonyl chloride (0.40 g, 1.56 mmol) and cyclohexylamine (0.46 mL, 3.90 mmol) were stirred together in dry dichloromethane (5 mL) for 16 hours. 4-bromo-N-cyclohexylbenzenesulfonamide (0.13 g) was provided after purification. MS (ESI) m/z 318. HPLC purity 100.0% at 210-370 nm, 10.0 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclohexylbenzenesulfonamide (127 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 µL, 0.02 mmol, 10 wt % in hexane) was added and the reaction was stirred for 16 hours. 4-(5-cyano-1-methyl-1H-pyrrol-2-yl)-N-cyclohexylbenzenesulfonamide (2 mg, 1%) was provided after purification. MS (ESI) m/z 343. HPLC purity 99.1% at 210-370 nm, 11.3 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 16

Preparation of 4-(5-cyano-1-methyl-1H-pyrrol-2-yl)-N-(2,2,2-trifluoroethyl)benzenesulfonamide

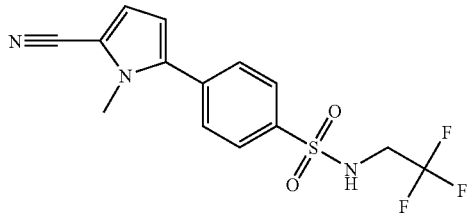

Step 1: According to general procedure C, 4-Bromobenzene sulfonyl chloride (0.40 g, 1.56 mmol) and 2,2,2-trifluoroethylamine (0.32 mL, 3.90 mmol) were stirred together in dry dichloromethane (5 mL) for 16 hours. 4-bromo-N-(2,2,2-trifluoroethyl)benzenesulfonamide (0.13 g) was provided after purification. MS (ESI) m/z 318. HPLC purity 100.0% at 210-370 nm, 8.7 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-(2,2,2-trifluoroethyl)benzenesulfonamide (127 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 µL, 0.02 mmol, 10 wt % in hexane) was added and the reaction was stirred for 16 hours. 4-(5-cyano-1-methyl-1H-pyrrol-2-yl)-N-(2,2,2-trifluoroethyl)benzenesulfonamide (57 mg, 42%) was provided after purification. MS (ESI) m/z 343. HPLC purity 97.2% at 210-370 nm, 10.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 17

Preparation of 4-(5-cyano-1-methyl-1H-pyrrol-2-yl)-N-(cyclopropylmethyl)benzenesulfonamide

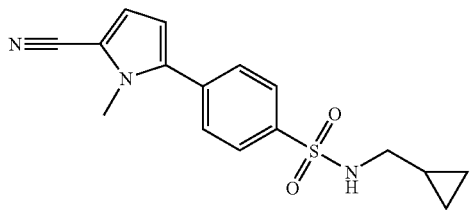

Step 1: According to general procedure C, 4-Bromobenzene sulfonyl chloride (0.40 g, 1.56 mmol) and cyclopropylmethylamine (0.35 mL, 3.90 mmol) were stirred together in dry dichloromethane (5 mL) for 16 hours. 4-bromo-N-(cyclopropylmethyl)benzenesulfonamide (0.12 g) was provided after purification. MS (ESI) m/z 290. HPLC purity 100.0% at 210-370 nm, 9.0 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-(cyclopropylmethyl)benzenesulfonamide (116 mg, 0.40 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 4-(5-cyano-1-methyl-1H-pyrrol-2-yl)-N-(cyclopropylmethyl)benzenesulfonamide (6 mg, 5%) was provided after purification. MS (ESI) m/z 315. HPLC purity 100.0% at 210-370 mn, 10.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 18

Preparation of 1-methyl-5-[4-(1H-pyrrol-1-ylsulfonyl)phenyl]-1H-pyrrole-2-carbonitrile

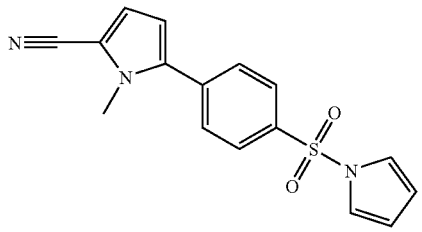

Step 1: Pyrrole (1.05 mL, 15.0 mmol) was added to a slurry of sodium hydride (0.71 g, 60% in mineral oil, 17.8 mmol) in dry THF (10 mL) at room temperature. 4-Bromobenzene sulfonyl chloride (1.5 g, 6.0 mmol) dissolved in dry THF (5 mL) was added dropwise. The reaction mixture was stirred overnight. The reaction was quenched with saturated ammonium chloride and diluted with ethyl acetate. The layers were separated and the organic layer was washed with water and brine. The organic layer was dried over anhydrous sodium sulfate, filtered and concentrated in vacuo to give the crude product. The crude product was purified via Isco chromatography (the Redisep™ column, silica, gradient 5-50% ethyl acetate in hexane) to give 1-[(4-bromophenyl)sulfonyl]-1H-pyrrole (0.27 g, 16%). MS (ESI) m/z 286. HPLC purity 100.0% at 210-370 nm, 9.9 min.; the Xterra® RP18 column, 3.5μ, 150×4.6 mm column 1.2 mL/min., 85/15-5/95 (ammonium formate buffer pH=3.5/ACN+MeOH) for 10 min., hold 4 min.

Step 2: According to general procedure B, 1-[(4-bromophenyl)sulfonyl]-1H-pyrrole (250 mg, 0.87 mmol), 5-cyano-1-methyl-1H-pyrrol-2-ylboronic acid (72 mg, 0.48 mmol), potassium fluoride (76 mg, 1.3 mmol), and tris(dibenzylideneacetone)dipalladium(0) (10 mg, 0.01 mmol) were placed in an oven dried flask under nitrogen and dry THF (1.0 mL) was added. Tri-t-butylphosphine (60 μL, 0.02 mmol, 10 wt % in hexane) was added and the reaction was stirred for 16 hours. 1-methyl-5-[4-(1H-pyrrol-1-ylsulfonyl)phenyl]-1H-pyrrole-2-carbonitrile (81 mg, 30%) was provided after purification. MS (ESI) m/z 311. HPLC purity 100.0% at 210-370 nm, 11.6 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 19

Preparation of 4-(5-cyano-1-methyl-1H-pyrrol-2-yl)-2-(trifluoromethyl)benzenesulfonamide

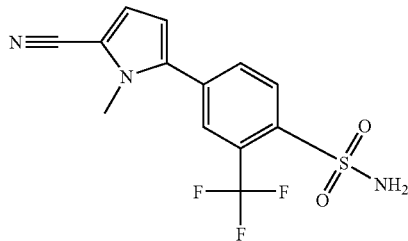

Step 1: 4-Bromo-2-trifluoromethyl-benzenesulfonyl chloride (0.50 g, 1.54 mmol) and ammonia (10 mL, ca. 7 N in methanol) were stirred in a sealed tube for 16 hours. The reaction solution was concentrated in vacuo onto the Celite® reagent. The crude product was purified via Isco chromatography (the Redisep™ column, silica, gradient 5-50% ethyl acetate in hexane) to recover 4-bromo-2-(trifluoromethyl)benzenesulfonamide (0.46 g, 96%). MS (ESI) m/z 304. HPLC purity 99.8% at 210-370 nm, 7.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-2-(trifluoromethyl)benzenesulfonamide (170 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-2-(trifluoromethyl)benzenesulfonamide (34 mg, 18%) was provided after purification. MS (ESI) m/z 329. HPLC purity 98.6% at 210-370 nm, 9.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 20

Preparation of 4-(5-cyano-1-methyl-1H-pyrrol-2-yl)-N,N-dimethyl-2-(trifluoromethyl)benzenesulfonamide

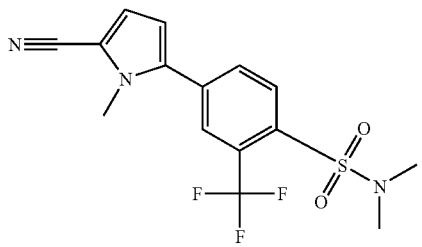

Step 1: In an analogous manner to General Procedure A, 4-Bromo-2-trifluoromethylbenzenesulfonyl chloride (0.50 g, 1.54 mmol) and dimethylamine (10 mL, 33% in ethanol) were stirred in sealed tube for 16 hours. 4-bromo-N,N-dimethyl-2-(trifluoromethyl)benzenesulfonamide (0.41 g, 80%) was provided after purification. MS (ESI) m/z 332. HPLC purity 100.0% at 210-370 nm, 9.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N,N-dimethyl-2-(trifluoromethyl)benzenesulfonamide (186 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-N,N-dimethyl-2-(trifluoromethyl)benzenesulfonamide (115 mg, 58%) was provided after purification. MS (ESI) m/z 357. HPLC purity 98.4% at 210-370 nm, 10.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 21

Preparation of 4-(5-cyano-1-methyl-1H-pyrrol-2-yl)-N-methyl-2-(trifluoromethyl)benzenes

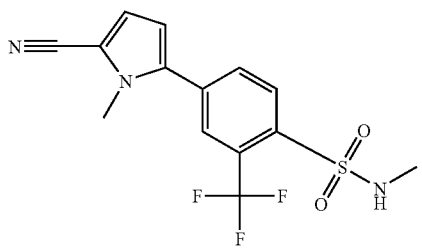

Step 1: In an analogous manner to General Procedure A, 4-Bromo-2-trifluoromethylbenzenesulfonyl chloride (0.50 g, 1.54 mmol) and methylamine (10 mL, 33% in ethanol) were stirred in sealed tube for 16 hours. 4-bromo-N-methyl-2-(trifluoromethyl)benzenesulfonamide (0.44 g, 90%) was provided after purification. MS (ESI) m/z 318. HPLC purity 100.0% at 210-370 nm, 8.5 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-methyl-2-(trifluoromethyl)benzenesulfonamide (178 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-N-methyl-2-(trifluoromethyl)benzenesulfonamide (90 mg, 47%) was provided after purification. MS (ESI) m/z 343. HPLC purity 99.2% at 210-370 nm, 9.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 22

Preparation of 4-(5-cyano-1-methyl-1H-pyrrol-2-yl)-N,N-diethyl-2-(trifluoromethyl)benzenesulfonamide

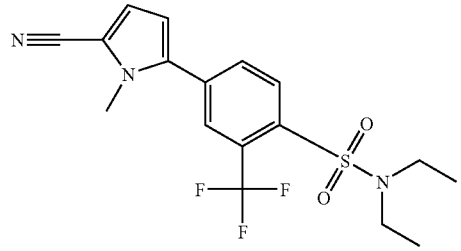

Step 1: According to general procedure C, 4-Bromo-2-trifluoromethyl-benzenesulfonyl chloride (0.50 g, 1.54 mmol) and diethylamine (0.40 mL, 3.85 mmol) were stirred together in dry dichloromethane (2 mL) for 16 hours. 4-bromo-N,N-diethyl-2-(trifluoromethyl)benzenesulfonamide (0.46 g, 83%) was provided after purification. MS (ESI) m/z 360. HPLC purity 100.0% at 210-370 nm, 10.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N,N-diethyl-2-(trifluoromethyl)benzenesulfonamide (201 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-N,N-diethyl-2-(trifluoromethyl)benzenesulfonamide (100 mg, 46%) was provided after purification. MS (ESI) m/z 385. HPLC purity 100.0% at 210-370 nm, 11.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 23

Preparation of 4-(5-cyano-1-methyl-1H-pyrrol-2-yl)-N-isopropyl-2-(trifluoromethyl)benzenesulfonamide

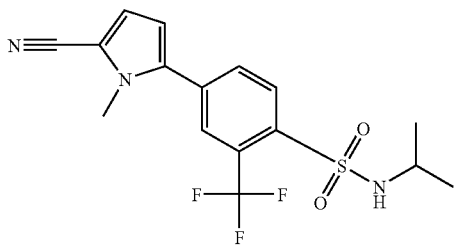

Step 1: According to general procedure C, 4-Bromo-2-trifluoromethyl-benzenesulfonyl chloride (0.50 g, 1.54 mmol) and isopropylamine (0.35 mL, 3.85 mmol) were stirred together in dry dichloromethane (2 mL) for 16 hours. 4-bromo-N-isopropyl-2-(trifluoromethyl)benzenesulfonamide (0.50 g, 95%) was provided after purification. MS (ESI) m/z 346. HPLC purity 100.0% at 210-370 nm, 9.6 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-isopropyl-2-(trifluoromethyl)benzenesulfonamide (193 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-N-isopropyl-2-(trifluoromethyl)benzenesulfonamide (91 mg, 44%) was provided after purification. MS (ESI) m/z 371. HPLC purity 100.0% at 210-370 nm, 10.6 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 24

Preparation of 4-(5-cyano-1-methyl-1H-pyrrol-2-yl)-N-ethyl-2-(trifluoromethyl)benzenesulfonamide

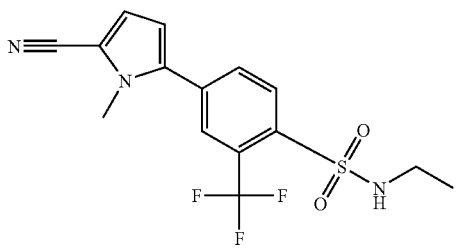

Step 1: According to general procedure C, 4-Bromo-2-trifluoromethyl-benzenesulfonyl chloride (0.50 g, 1.54 mmol) and ethylamine (2.0 mL, 2.0 M in THF, 4.00 mmol) were stirred together in dry dichloromethane (2 mL) for 16 hours. 4-bromo-N-ethyl-2-(trifluoromethyl)benzenesulfonamide (0.50 g, 98%) was provided after purification. MS (ESI) m/z 332. HPLC purity 100.0% at 210-370 nm, 9.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-ethyl-2-(trifluoromethyl)benzenesulfonamide (186 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-N-ethyl-2-(trifluoromethyl)benzenesulfonamide (90 mg, 45%) was provided after purification. MS (ESI) m/z 357. HPLC purity 100.0% at 210-370 nm, 10.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 25

Preparation of 4-(5-cyano-1-methyl-1H-pyrrol-2-yl)-N-propyl-2-(trifluoromethyl)benzenesulfonamide

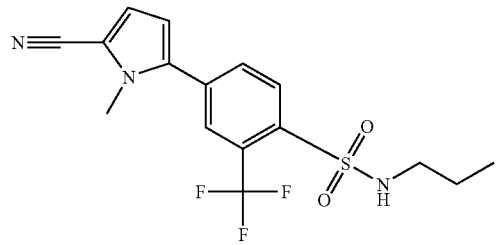

Step 1: According to general procedure C, 4-Bromo-2-trifluoromethyl-benzenesulfonyl chloride (0.50 g, 1.54 mmol) and propylamine (0.32 mL, 3.85 mmol) were stirred together in dry dichloromethane (2 mL) for 16 hours. 4-bromo-N-propyl-2-(trifluoromethyl)benzenesulfonamide (0.53 g, 100%) was provided after purification. MS (ESI) m/z 346. HPLC purity 100.0% at 210-370 nm, 9.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-propyl-2-(trifluoromethyl)benzenesulfonamide (193 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-N-propyl-2-(trifluoromethyl)benzenesulfonamide (68 mg, 33%) was provided after purification. MS (ESI) m/z 371. HPLC purity 100.0% at 210-370 nm, 10.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 26

Preparation of 1-methyl-5-[4-(pyrrolidin-1-ylsulfonyl)-3-(trifluoromethyl)phenyl]-1H-pyrrole-2-carbonitrile

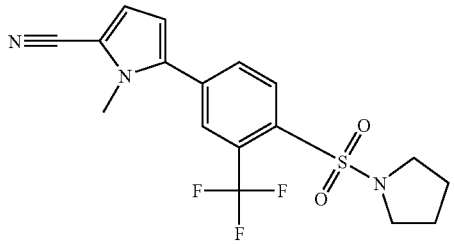

Step 1: According to general procedure C, 4-Bromo-2-trifluoromethyl-benzenesulfonyl chloride (0.50 g, 1.54 mmol) and pyrrolidine (0.32 mL, 3.85 mmol) were stirred together in dry dichloromethane (2 mL) for 16 hours. 1-{[4-bromo-2-(trifluoromethyl)phenyl]sulfonyl}pyrrolidine (0.53 g, 96%) was provided after purification. MS (ESI) m/z 358. HPLC purity 100.0% at 210-370 nm, 9.8 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: In analogous manner to general procedure B, 1-{[4-bromo-2-(trifluoromethyl)phenyl]sulfonyl}pyrrolidine (200 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 µL, 0.02 mmol, 10 wt % in hexane) was added and the reaction was stirred for 16 hours. 1-methyl-5-[4-(pyrrolidin-1-ylsulfonyl)-3-(trifluoromethyl)phenyl]-1H-pyrrole-2-carbonitrile (117 mg, 54%) was provided after purification. HRMS: calcd for $C_{17}H_{16}F_3N_3O_2S+H^+$, 384.09881; found (ESI, [M+H]$^+$), 384.0991, HPLC purity 100.0% at 210-370 nm, 10.9 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 27

Preparation of 4-(5-cyano-1-methyl-1H-pyrrol-2-yl)-N-cyclopropyl-2-(trifluoromethyl)benzenesulfonamide

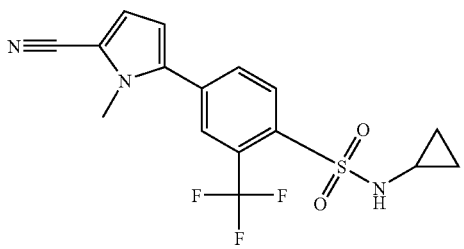

Step 1: According to general procedure C, 4-Bromo-2-trifluoromethyl-benzenesulfonyl chloride (0.50 g, 1.54 mmol) and cyclopropylamine (0.27 mL, 3.85 mmol) were stirred together in dry dichloromethane (2 mL) for 16 hours. 4-bromo-N-cyclopropyl-2-(trifluoromethyl)benzenesulfonamide (0.51 g, 96%) was provided after purification. MS (ESI) m/z 344. HPLC purity 100.0% at 210-370 nm, 9.3 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclopropyl-2-(trifluoromethyl)benzenesulfonamide (193 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 µL, 0.02 mmol, 10 wt % in hexane) was added and the reaction was stirred for 16 hours. 4-(5-cyano-1-methyl-1H-pyrrol-2-yl)-N-cyclopropyl-2-(trifluoromethyl)benzenesulfonamide was provided (87 mg, 42%) after purification. MS (ESI) m/z 369. HPLC purity 99.6% at 210-370 nm, 10.3 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 28

Preparation of 4-(5-cyano-1-methyl-1H-pyrrol-2-yl)-N-(cyclopropylmethyl)-2-(trifluoromethyl)benzenesulfonamide

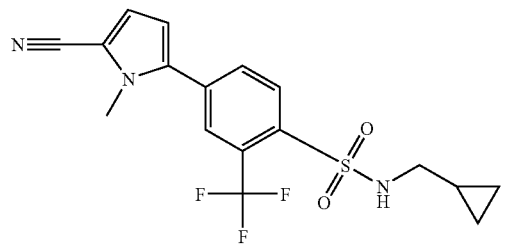

Step 1: According to general procedure C, 4-Bromo-2-trifluoromethyl-benzenesulfonyl chloride (0.50 g, 1.54 mmol) and cyclopropylmethylamine (0.34 mL, 3.85 mmol) were stirred together in dry dichloromethane (2 mL) for 16 hours. 4-bromo-N-(cyclopropylmethyl)-2-(trifluoromethyl)-benzenesulfonamide (0.50 g, 91%) was provided after purification. MS (ESI) m/z 358. HPLC purity 100.0% at 210-370 nm, 9.8 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: In analogous manner to general procedure B, 4-bromo-N-(cyclopropylmethyl)-2-(trifluoromethyl)benzenesulfonamide (200 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 µL, 0.02 mmol, 10 wt % in hexane) was added and the reaction was stirred for 16 hours. 4-(5-cyano-1-methyl-1H-pyrrol-2-yl)-N-(cyclopropylmethyl)-2-(trifluoromethyl)-benzenesulfonamide (106 mg, 53%) was provided after purification. MS (ESI) m/z 383. HPLC purity 100.0% at 210-370 nm, 10.8 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 29

Preparation of 4-(5-cyano-1-methyl-1H-pyrrol-2-yl)-N-cyclobutyl-2-(trifluoromethyl)benzenesulfonamide

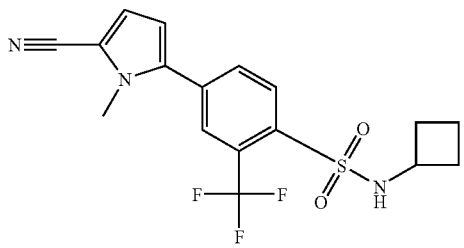

Step 1: According to general procedure C, 4-Bromo-2-trifluoromethyl-benzenesulfonyl chloride (0.50 g, 1.54 mmol) and cyclobutylamine (0.33 mL, 3.85 mmol) were stirred together in dry dichloromethane (2 mL) for 16 hours. 4-bromo-N-cyclobutyl-2-(trifluoromethyl)benzenesulfonamide (0.53 g, 96%) was provided after purification. MS (ESI) m/z 358. HPLC purity 100.0% at 210-370 nm, 9.9 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclobutyl-2-(trifluoromethyl)benzenesulfonamide (200 mg, 0.56 mmol), 5-cyano-1-methyl-1H-pyrrol-2-ylboronic acid (100 mg, 0.67 mmol), potassium fluoride (107 mg, 1.85 mmol), and tris(dibenzylideneacetone)dipalladium(0) (14 mg, 0.01 mmol) were placed in an oven dried flask under nitrogen and dry THF (1.4 mL) was added. Tri-t-butylphosphine (83 μL, 0.02 mmol, 10 wt % in hexane) was added and the reaction was stirred for 16 hours. 4-(5-cyano-1-methyl-1H-pyrrol-2-yl)-N-cyclobutyl-2-(trifluoromethyl)benzenesulfonamide (122 mg, 57%) was provided after purification. MS (ESI) m/z 383. HPLC purity 99.3% at 210-370 nm, 10.9 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 30

Preparation of 4-(5-cyano-1-methyl-1H-pyrrol-2-yl)-3-fluorobenzenesulfonamide

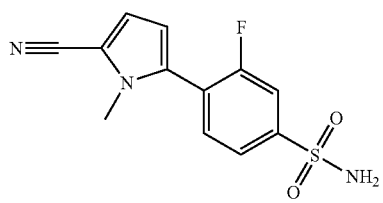

Step 1: According to general procedure A, 4-Bromo-3-fluoro-benzenesulfonyl chloride (0.40 g, 1.46 mmol) and ammonia (20 mL, ca. 7N in methanol) were stirred together for 16 hours. 4-bromo-3-fluorobenzenesulfonamide was provided after purification (0.23 g, 61%). HRMS: calcd for $C_6H_5BrFNO_2S$, 252.92084; found (EI, M+), 252.9201. HPLC purity 100.0% at 210-370 nm, 7.5 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-3-fluorobenzenesulfonamide (150 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-3-fluorobenzenesulfonamide (29 mg, 18%) was provided after purification. MS (ESI) m/z 279. HPLC purity 100.0% at 210-370 nm, 8.6 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 31

Preparation of 4-(5-cyano-1-methyl-1H-pyrrol-2-yl)-3-fluoro-N-methylbenzenesulfonamide

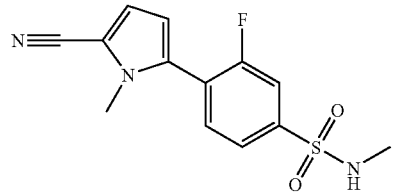

Step 1: According to general procedure A, 4-Bromo-3-fluoro-benzenesulfonyl chloride (0.40 g, 1.46 mmol) and methylamine (10 mL, 33% in ethanol) were stirred together for 16 hours. 4-bromo-3-fluoro-N-methylbenzenesulfonamide (0.33 g, 85%) was provided after purification. HRMS: calcd for $C_7H_7BrFNO_2S$, 266.93649; found (EI, M+.), 266.9376. HPLC purity 100.0% at 210-370 nm, 8.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-3-fluoro-N-methylbenzenesulfonamide (158 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-3-fluoro-N-methylbenzenesulfonamide (53 mg, 31%) was provided after purification. HRMS: calcd for $C_{13}H_{12}FN_3O_2S$, 293.06342; found (EI, M+.), 293.0627. HPLC purity 99.5% at 210-370 nm, 8.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 32

Preparation of 4-(5-cyano-1-methyl-1H-pyrrol-2-yl)-3-fluoro-N,N-dimethylbenzenesulfonamide

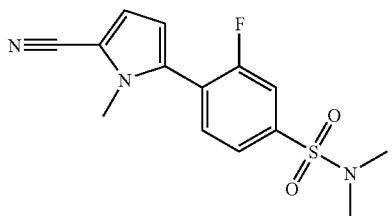

Step 1: According to general procedure A, 4-Bromo-3-fluoro-benzenesulfonyl chloride (0.40 g, 1.46 mmol) and dimethylamine (10 mL, 33% in ethanol) were stirred together for 16 hours. 4-bromo-3-fluoro-N,N-dimethylbenzenesulfonamide (0.36 g, 89%) was provided after purification. HRMS: calcd for $C_8H_9BrFNO_2S$, 280.95214; found (EI, M$^+$.), 280.9516. HPLC purity 98.9% at 210-370 nm, 9.6 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-3-fluoro-N,N-dimethylbenzenesulfonamide (166 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-3-fluoro-N,N-dimethylbenzenesulfonamide (51 mg, 28%) was provided after purification. HRMS: calcd for $C_{14}H_{14}FN_3O_2S$, 307.07907; found (EI, M$^+$.), 307.0786. HPLC purity 99.3% at 210-370 nm, 8.8 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 33

Preparation of 4-(5-cyano-1-methyl-1H-pyrrol-2-yl)-N-ethyl-3-fluorobenzenesulfonamide

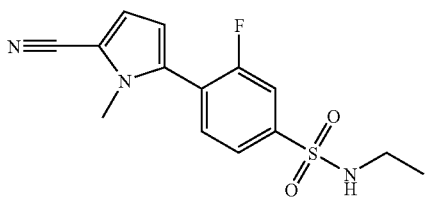

Step 1: According to general procedure A, 4-Bromo-3-fluoro-benzenesulfonyl chloride (0.40 g, 1.46 mmol) and ethylamine (5 mL, 10.0 mmol, 2.0 M in THF) were stirred together for 16 hours. 4-bromo-N-ethyl-3-fluorobenzenesulfonamide (0.38 g, 92%) was provided after purification. HRMS: calcd for $C_8H_9BrFNO_2S$, 280.95214; found (EI, M$^+$.), 280.951. HPLC purity 100.0% at 210-370 nm, 9.6 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-ethyl-3-fluorobenzenesulfonamide (166 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N-ethyl-3-fluorobenzenesulfonamide (44 mg, 24%) was provided after purification. HRMS: calcd for $C_{14}H_{14}FN_3O_2S$, 307.07907; found (EI, M$^+$.), 307.0792. HPLC purity 99.5% at 210-370 nm, 8.7 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 34

Preparation of 4-(5-cyano-1-methyl-1H-pyrrol-2-yl)-N,N-diethyl-3-fluorobenzenesulfonamide

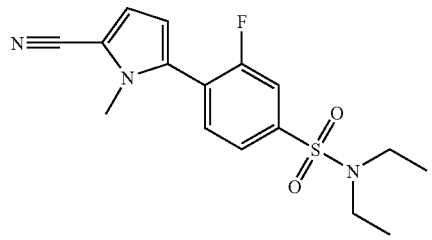

Step 1: According to general procedure C, 4-Bromo-3-fluoro-benzenesulfonyl chloride (0.40 g, 1.46 mmol) and diethylamine (0.38 mL, 3.65 mmol) were stirred together with dry dichloromethane (5 mL) for 16 hours. 4-bromo-N,N-diethyl-3-fluorobenzenesulfonamide (0.41 g, 90%) was provided after purification. HRMS: calcd for $C_{10}H_{13}BrFNO_2S$, 308.98344; found (EI, M$^+$.), 308.9822. HPLC purity 100.0% at 210-370 nm, 10.9 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N,N-diethyl-3-fluorobenzenesulfonamide (183 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N,N-diethyl-3-fluorobenzenesulfonamide (46 mg, 23%) was provided after purification. HRMS: calcd for $C_{16}H_{18}FN_3O_2S+H^+$, 336.11765; found (ESI, [M+H]$^+$), 336.117. HPLC purity 99.7% at 210-370 nm, 9.7 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 35

Preparation of 4-(5-cyano-1-methyl-1H-pyrrol-2-yl)-3-fluoro-N-isopropylbenzenesulfonamide

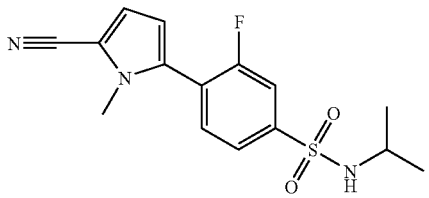

Step 1: According to general procedure C, 4-Bromo-3-fluoro-benzenesulfonyl chloride (0.40 g, 1.46 mmol) and isopropylamine (0.31 mL, 3.65 mmol) were stirred together with dry dichloromethane (5 mL) for 16 hours. 4-bromo-3-fluoro-N-isopropylbenzenesulfonamide (0.40 g, 93%) was provided after purification. HRMS: calcd for $C_9H_{11}BrFNO_2S$, 294.96779; found (EI, $M^+$.), 294.9665. HPLC purity 100.0% at 210-370 nm, 10.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-3-fluoro-N-isopropylbenzenesulfonamide (174 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-3-fluoro-N-isopropylbenzenesulfonamide (35 mg, 19%) was provided after purification. HRMS: calcd for $C_{15}H_{16}FN_3O_2S$, 321.09472; found (EI, $M^+$.), 321.0948. HPLC purity 100.0% at 210-370 nm, 9.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 36

Preparation of 4-(5-cyano-1-methyl-1H-pyrrol-2-yl)-3-fluoro-N-propylbenzenesulfonamide

Step 1: According to general procedure C, 4-Bromo-3-fluoro-benzenesulfonyl chloride (0.40 g, 1.46 mmol) and propylamine (0.30 mL, 3.65 mmol) were stirred together with dry dichloromethane (5 mL) for 16 hours. 4-bromo-3-fluoro-N-propylbenzenesulfonamide (0.39 g, 90%) was provided after purification. HRMS: calcd for $C_9H_{11}BrFNO_2S$, 294.96779; found (EI, $M^+$.), 294.9684. HPLC purity 100.0% at 210-370 nm, 10.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-3-fluoro-N-propylbenzenesulfonamide (174 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-Cyano-1-methyl-1H-pyrrol-2-yl)-3-fluoro-N-propylbenzenesulfonamide was provided after purification. HRMS: calcd for $C_{15}H_{16}FN_3O_2S$, 321.09472; found (EI, $M^+$.), 321.0947. HPLC purity 99.7% at 210-370 nm, 9.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 37

Preparation of 5-[2-fluoro-4-(pyrrolidin-1-ylsulfonyl)phenyl]-1-methyl-1H-pyrrole-2-carbonitrile

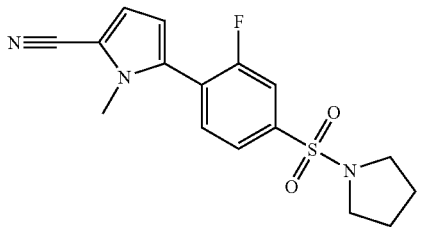

Step 1: According to general procedure C, 4-Bromo-3-fluoro-benzenesulfonyl chloride (0.40 g, 1.46 mmol) and pyrrolidine (0.30 mL, 3.65 mmol) were stirred together with dry dichloromethane (5 mL) for 16 hours. 1-[(4-bromo-3-fluorophenyl)sulfonyl]pyrrolidine (0.43 g, 96%) was provided after purification. HRMS: calcd for $C_{10}H_{11}BrFNO_2S$, 306.96779; found (EI, $M^+$.), 306.968. HPLC purity 100.0% at 210-370 nm, 10.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 1-[(4-bromo-3-fluorophenyl)sulfonyl]pyrrolidine (182 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 5-[2-fluoro-4-(pyrrolidin-1-ylsulfonyl)phenyl]-1-methyl-1H-pyrrole-2-carbonitrile (61 mg, 31%) was provided after purification. HRMS: calcd for $C_{16}H_{16}FN_3O_2S+H^+$, 334.10200; found (ESI, $[M+H]^+$), 334.1035. HPLC purity 100.0% at 210-370 nm, 9.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 38

Preparation of 4-(5-cyano-1-methyl-1H-pyrrol-2-yl)-N-cyclopropyl-3-fluorobenzenesulfonamide

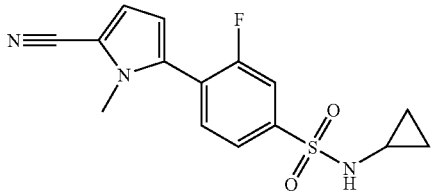

Step 1: According to general procedure C, 4-Bromo-3-fluoro-benzenesulfonyl chloride (0.40 g, 1.46 mmol) and cyclopropylamine (0.25 mL, 3.65 mmol) were stirred together with dry dichloromethane (5 mL) for 16 hours. 4-bromo-N-cyclopropyl-3-fluorobenzenesulfonamide (0.37 g, 86%) was provided after purification. HRMS: calcd for $C_9H_9BrFNO_2S-H^+$, 291.94486; found (ESI, $[M-H]^-$), 291.9462. HPLC purity 100.0% at 210-370 nm, 9.8 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclopropyl-3-fluorobenzenesulfonamide (175 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N-cyclopropyl-3-fluorobenzenesulfonamide (26 mg, 14%) was provided after purification. MS (ESI) m/z 319. HPLC purity 100.0% at 210-370 nm, 8.9 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 39

Preparation of 4-(5-cyano-1-methyl-1H-pyrrol-2-yl)-N-(cyclopropylmethyl)-3-fluorobenzenesulfonamide

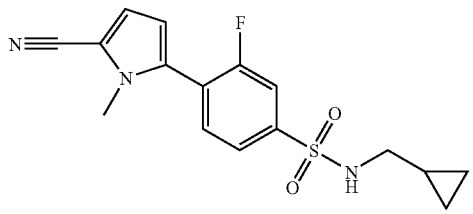

Step 1: According to general procedure C, 4-Bromo-3-fluoro-benzenesulfonyl chloride (0.40 g, 1.46 mmol) and cyclopropylmethylamine (0.32 mL, 3.65 mmol) were stirred together with dry dichloromethane (5 mL) for 16 hours. 4-bromo-N-(cyclopropylmethyl)-3-fluorobenzenesulfonamide (0.25 g, 55%) was provided after purification. HRMS: calcd for $C_{10}H_{11}BrFNO_2S-H^+$, 305.96051; found (ESI, $[M-H]^-$), 305.9603. HPLC purity 100.0% at 210-370 nm, 10.5 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-(cyclopropylmethyl)-3-fluorobenzenesulfonamide (182 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N-(cyclopropylmethyl)-3-fluorobenzenesulfonamide (26 mg, 13%) was provided after purification. HRMS: calcd for $C_{16}H_{16}FN_3O_2S+H^+$, 334.10200; found (ESI, $[M+H]^+$), 334.1024. HPLC purity 100.0% at 210-370 nm, 9.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 40

Preparation of 4-(5-cyano-1-methyl-1H-pyrrol-2-yl)-N-cyclobutyl-3-fluorobenzenesulfonamide

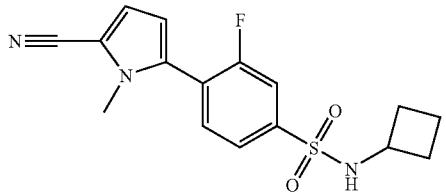

Step 1: According to general procedure C, 4-Bromo-3-fluoro-benzenesulfonyl chloride (0.40 g, 1.46 mmol) and cyclobutylamine (0.31 mL, 3.65 mmol) were stirred together with dry dichloromethane (5 mL) for 16 hours. 4-bromo-N-cyclobutyl-3-fluorobenzenesulfonamide (0.40 g, 89%) was provided after purification. MS (ESI) m/z 308. HPLC purity 98.2% at 210-370 nm, 10.6 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclobutyl-3-fluorobenzenesulfonamide (182 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N-cyclobutyl-3-fluorobenzenesulfonamide (28 mg, 14%) was provided after purification. HRMS: calcd for $C_{16}H_{16}FN_3O_2S-H^+$, 332.08745; found (ESI, $[M-H]^-$), 332.0867. HPLC purity 96.9% at 210-370 nm, 9.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 41

Preparation of 4-(5-cyano-1-methyl-1H-pyrrol-2-yl)-N,N-diethyl-2-fluorobenzenesulfonamide

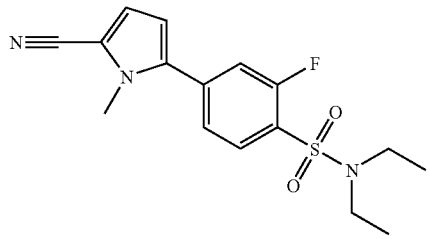

Step 1: According to general procedure C, 4-Bromo-2-fluoro-benzenesulfonyl chloride (0.40 g, 1.46 mmol) and diethylamine (0.38 mL, 3.65 mmol) were stirred together with dry dichloromethane (5 mL) for 16 hours. 4-bromo-N,N-diethyl-2-fluorobenzenesulfonamide (0.19 g, 43%) was provided after purification. HRMS: calcd for $C_{10}H_{13}BrFNO_2S+H^+$, 309.99071; found (ESI, [M+H]$^+$), 309.9917. HPLC purity 100.0% at 210-370 nm, 9.6 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N,N-diethyl-2-fluorobenzenesulfonamide (183 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N,N-diethyl-2-fluorobenzenesulfonamide (63 mg, 32%) was provided after purification. MS (ESI) m/z 335. HPLC purity 100.0% at 210-370 nm, 9.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 42

Preparation of 4-(5-cyano-1-methyl-1H-pyrrol-2-yl)-2-fluoro-N-isopropylbenzenesulfonamide

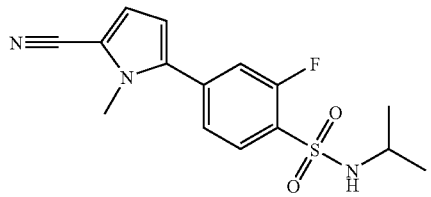

Step 1: According to general procedure C, 4-Bromo-2-fluoro-benzenesulfonyl chloride (0.40 g, 1.46 mmol) and isopropylamine (0.31 mL, 3.65 mmol) were stirred together with dry dichloromethane (5 mL) for 16 hours. 4-bromo-2-fluoro-N-isopropylbenzenesulfonamide (189 mg, 44%) was provided after purification. MS (ESI) m/z 296. HPLC purity 100.0% at 210-370 nm, 10.6 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-2-fluoro-N-isopropylbenzenesulfonamide (177 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-2-fluoro-N-isopropylbenzenesulfonamide (24 mg, 13%) was provided after purification. MS (ESI) m/z 321. HPLC purity 100.0% at 210-370 nm, 9.0 min.; the Xterrag RP18 column, 3.5μ, 150×4.6 mm column, 1.2 mL/min., 85/15-5/95 (ammonium formate buffer pH=3.5/ACN+MeOH) for 10 min., hold 4 min.

Example 43

Preparation of 4-(5-cyano-1-methyl-1H-pyrrol-2-yl)-N-cyclopropyl-2-fluorobenzenesulfonamide

Step 1: According to general procedure C, 4-Bromo-2-fluoro-benzenesulfonyl chloride (0.40 g, 1.46 mmol) and cyclopropylamine (0.25 mL, 3.65 mmol) were stirred together with dry dichloromethane (5 mL) for 16 hours. 4-bromo-N-cyclopropyl-2-fluorobenzenesulfonamide (190 mg, 44%) was provided after purification. MS (ESI) m/z 294. HPLC purity 98.6% at 210-370 nm, 10.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclopropyl-2-fluorobenzenesulfonamide (176 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N-cyclopropyl-2-fluorobenzenesulfonamide (45 mg, 24%) was provided after purification. MS (ESI) m/z 319. HPLC purity 100.0% at 210-370 nm, 8.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 44

Preparation of 4-(5-cyano-1-methyl-1H-pyrrol-2-yl)-N-(cyclopropylmethyl)-2-fluorobenzenesulfonamide

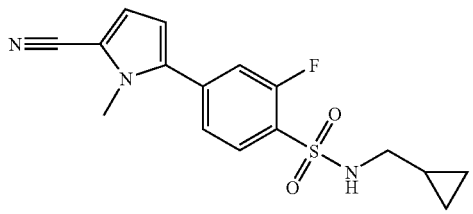

Step 1: According to general procedure C, 4-Bromo-2-fluoro-benzenesulfonyl chloride (0.40 g, 1.46 mmol) and cyclopropylmethylamine (0.31 mL, 3.65 mmol) were stirred together with dry dichloromethane (5 mL) for 16 hours. 4-bromo-N-(cyclopropylmethyl)-2-fluorobenzenesulfonamide (0.18 g, 40%) was provided after purification. MS (ESI) m/z 308. HPLC purity 97.7% at 210-370 nm, 10.7 min.; the Xterra® RP18 column, 3.5μ, 150×4.6 mm column, 1.2 mL/min., 85/15-5/95 (Ammonium Bicarb Buff. pH=9.5/ACN+MeOH) for 10 min., hold 4 min.

Step 2: According to general procedure B, 4-bromo-N-(cyclopropylmethyl)-2-fluorobenzenesulfonamide (181 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N-(cyclopropylmethyl)-2-fluorobenzenesulfonamide (20 mg, 10%) was provided after purification. MS (ESI) m/z 333. HPLC purity 100.0% at 210-370 nm, 11.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 45

Preparation of 4-(5-cyano-1-methyl-1H-pyrrol-2-yl)-N-cyclobutyl-2-fluorobenzenesulfonamide

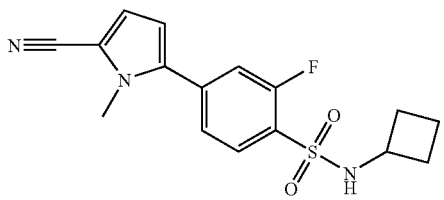

Step 1: According to general procedure C, 4-Bromo-2-fluoro-benzenesulfonyl chloride (0.40 g, 1.46 mmol) and cyclobutylamine (0.31 mL, 3.65 mmol) were stirred together with dry dichloromethane (5 mL) for 16 hours. 4-bromo-N-cyclobutyl-2-fluorobenzenesulfonamide (192 mg, 43%) was provided after purification. MS (ESI) m/z 308. HPLC purity 90.7% at 210-370 nm, 11.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclobutyl-2-fluorobenzenesulfonamide (185 mg, 0.59 mmol), 5-cyano-1-methyl-1H-pyrrol-2-ylboronic acid (106 mg, 0.70 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N-cyclobutyl-2-fluorobenzenesulfonamide (25 mg, 13%) was provided after purification. MS (ESI) m/z 333. HPLC purity 99.6% at 210-370 nm, 9.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 46

Preparation of 4-(5-cyano-1-methyl-1H-pyrrol-2-yl)-2-(trifluoromethoxy)benzenesulfonamide

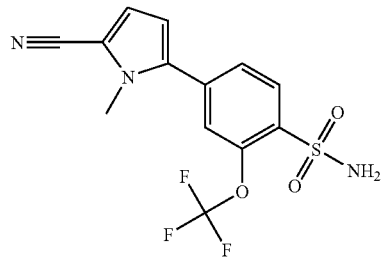

Step 1: According to general procedure A, 4-Bromo-2-trifluoromethoxy-benzenesulfonyl chloride (0.35 g, 1.03 mmol) and ammonia (10 mL, ca. 7N in methanol) were stirred together for 16 hours. 4-bromo-2-(trifluoromethoxy)benzenesulfonamide (0.33 g, 100%) was provided after purification. MS (ESI) m/z 320. HPLC purity 100.0% at 210-370 nm, 8.0 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-2-(trifluoromethoxy)benzenesulfonamide (192 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-2-(trifluoromethoxy)benzenesulfonamide (50 mg, 24%) was provided after purification. MS (ESI) m/z 345. HPLC purity 100.0% at 210-370 nm, 8.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 47

Preparation of 4-(5-cyano-1-methyl-1H-pyrrol-2-yl)-N-methyl-2-(trifluoromethoxy)benzenesulfonamide

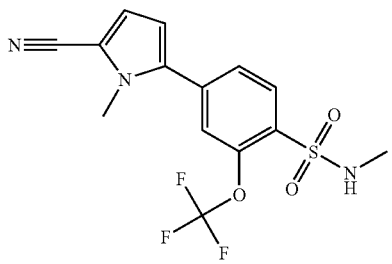

Step 1: According to general procedure A, 4-Bromo-2-trifluoromethoxy-benzenesulfonyl chloride (0.35 g, 1.03 mmol) and methylamine (10 mL, 33% in ethanol) were stirred in sealed tube for 16 hours. 4-bromo-N-methyl-2-(trifluoromethoxy)benzenesulfonamide (0.21 g, 61%) was provided after purification. MS (ESI) m/z 334. HPLC purity 98.0% at 210-370 nm, 8.8 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-methyl-2-(trifluoromethoxy)benzenesulfonamide (200 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N-methyl-2-(trifluoromethoxy)benzenesulfonamide (61 mg, 28%) was provided after purification. MS (ESI) m/z 359. HPLC purity 99.6% at 210-370 nm, 9.0 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 48

Preparation of 4-(5-cyano-1-methyl-1H-pyrrol-2-yl)-N,N-dimethyl-2-(trifluoromethoxy)benzenesulfonamide

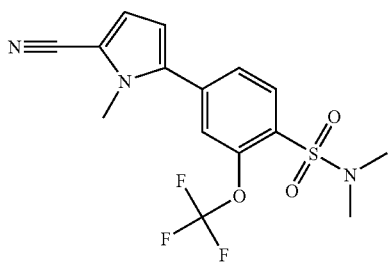

Step 1: According to general procedure A, 4-Bromo-2-trifluoromethoxy-benzenesulfonyl chloride (0.35 g, 1.03 mmol) and dimethylamine (10 mL, 33% in ethanol) were stirred in sealed tube for 16 hours. 4-Bromo-N,N-dimethyl-2-trifluoromethoxy-benzenesulfonamide (0.29 g, 81%) was provided after purification. Mp. 55-58° C. MS (ESI) m/z 348.14.

Step 2: According to general procedure B, 4-Bromo-N,N-dimethyl-2-trifluoromethoxy-benzenesulfonamide (209 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N,N-dimethyl-2-(trifluoromethoxy)benzenesulfonamide (73 mg, 32%) was provided after purification. MS (ESI) m/z 373. HPLC purity 99.1% at 210-370 nm, 9.7 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 49

Preparation of 4-(5-cyano-1-methyl-1H-pyrrol-2-yl)-N-ethyl-2-(trifluoromethoxy)benzenesulfonamide

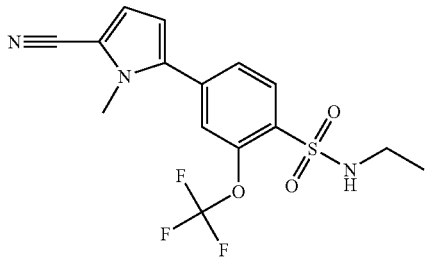

Step 1: According to general procedure A, 4-Bromo-2-trifluoromethoxy-benzenesulfonyl chloride (0.35 g, 1.03 mmol) and ethylamine (5 mL, 10.0 mmol, 2.0 M in THF) were stirred together for 16 hours. 4-bromo-N-ethyl-2-(trifluoromethoxy)benzenesulfonamide (0.23 g, 64%) was provided after purification. MS (ESI) m/z 348. HPLC purity 100.0% at 210-370 nm, 9.3 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-ethyl-2 (trifluoromethoxy)benzenesulfonamide (208 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N-ethyl-2-(trifluoromethoxy)benzenesulfonamide (40 mg, 18%) was provided after purification. MS (ESI) m/z 373. HPLC purity 99.4% at 210-370 nm, 9.4 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 50

Preparation of 4-(5-cyano-1-methyl-1H-pyrrol-2-yl)-N,N-diethyl-2-(trifluoromethoxy)benzenesulfonamide

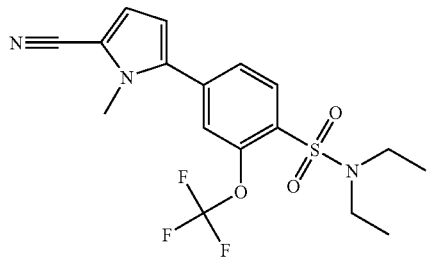

Step 1: According to general procedure C, 4-Bromo-2-trifluoromethoxy-benzenesulfonyl chloride (0.35 g, 1.03 mmol) and diethylamine (0.26 mL, 2.57 mmol) were stirred together with dry dichloromethane (5 mL) for 16 hours. 4-bromo-N,N-diethyl-2-(trifluoromethoxy)benzenesulfonamide (0.38 g, 98%) was provided after purification. MS (ESI) m/z 376. HPLC purity 100.0% at 210-370 nm, 10.4 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N,N-diethyl-2-(trifluoromethoxy)benzenesulfonamide (225 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N,N-diethyl-2-(trifluoromethoxy)benzenesulfonamide (98 mg, 42%) was provided after purification. MS (ESI) m/z 401. HPLC purity 100.0% at 210-370 nm, 10.3 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 51

Preparation of 4-(5-cyano-1-methyl-1H-pyrrol-2-yl)-N-isopropyl-2-(trifluoromethoxy)benzenesulfonamide

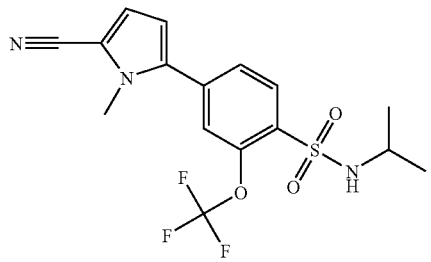

Step 1: According to general procedure C, 4-Bromo-2-trifluoromethoxy-benzenesulfonyl chloride (0.35 g, 1.03 mmol) and isopropylamine (0.21 mL, 2.57 mmol) were stirred together with dry dichloromethane (5 mL) for 16 hours. 4-bromo-N-isopropyl-2-(trifluoromethoxy)benzenesulfonamide (0.29 g, 78%) was provided after purification. MS (ESI) m/z 362. HPLC purity 100.0% at 210-370 nm, 9.8 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-isopropyl-2-(trifluoromethoxy)benzenesulfonamide (217 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N-isopropyl-2-(trifluoromethoxy)benzenesulfonamide (79 mg, 35%) was provided after purification. MS (ESI) m/z 387. HPLC purity 100.0% at 210-370 nm, 9.8 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 52

Preparation of 4-(5-cyano-1-methyl-1H-pyrrol-2-yl)-N-propyl-2-(trifluoromethoxy)benzenesulfonamide

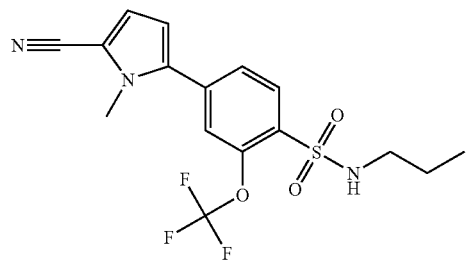

Step 1: According to general procedure C, 4-Bromo-2-trifluoromethoxy-benzenesulfonyl chloride (0.35 g, 1.03 mmol) and propylamine (0.21 mL, 2.57 mmol) were stirred together with dry dichloromethane (5 mL) for 16 hours. 4-bromo-N-propyl-2-(trifluoromethoxy)benzenesulfonamide (0.37 g, 91%) was provided after purification. MS (ESI) m/z 362. HPLC purity 100.0% at 210-370 nm, 9.9 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-propyl-2-(trifluoromethoxy)benzenesulfonamide (217 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N-propyl-2-(trifluoromethoxy)benzenesulfonamide (66 mg, 29%) was provided after purification. MS (ESI) m/z 387. HPLC purity 100.0% at 210-370 nm, 9.9 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 53

Preparation of 1-methyl-5-[4-(pyrrolidin-1-ylsulfonyl)-3-(trifluoromethoxy)phenyl]-1H-pyrrole-2-carbonitrile

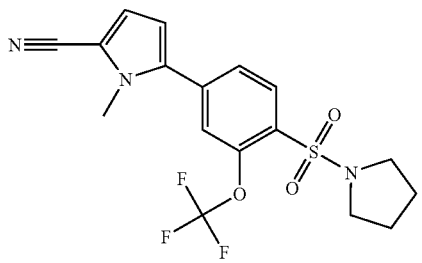

Step 1: According to general procedure C, 4-Bromo-2-trifluoromethoxy-benzenesulfonyl chloride (0.35 g, 1.03 mmol) and pyrrolidine (0.21 mL, 2.57 mmol) were stirred together with dry dichloromethane (5 mL) for 16 hours. 1-{[4-bromo-2-(trifluoromethoxy)phenyl]sulfonyl}pyrrolidine (0.25 g, 65%) was provided after purification. MS (ESI) m/z 374. HPLC purity 100.0% at 210-370 nm, 10.1 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-2-(trifluoromethoxy)phenyl]sulfonyl}pyrrolidine (224 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 1-methyl-5-[4-(pyrrolidin-1-ylsulfonyl)-3-(trifluoromethoxy)phenyl]-1H-pyrrole-2-carbonitrile (98 mg, 42%) was provided after purification. MS (ESI) m/z 399. HPLC purity 100.0% at 210-370 nm, 10.0 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 54

Preparation of 4-(5-cyano-1-methyl-1H-pyrrol-2-yl)-N-cyclopropyl-2-(trifluoromethoxy)benzenesulfonamide

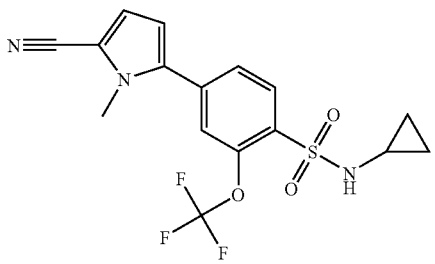

Step 1: According to general procedure C, 4-Bromo-2-trifluoromethoxy-benzenesulfonyl chloride (0.35 g, 1.03 mmol) and cyclopropylamine (0.17 mL, 2.57 mmol) were stirred together with dry dichloromethane (5 mL) for 16 hours. 4-bromo-N-cyclopropyl-2-(trifluoromethoxy)benzenesulfonamide (0.25 g, 68%) was provided after purification. MS (ESI) m/z 360. HPLC purity 100.0% at 210-370 nm, 9.5 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclopropyl-2-(trifluoromethoxy)benzenesulfonamide (216 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N-cyclopropyl-2-(trifluoromethoxy)benzenesulfonamide (65 mg, 29%) was provided after purification. MS (ESI) m/z 385. HPLC purity 99.2% at 210-370 nm, 9.5 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 55

Preparation of 4-(5-cyano-1-methyl-1H-pyrrol-2-yl)-N-(cyclopropylmethyl)-2-(trifluoromethoxy)benzenesulfonamide

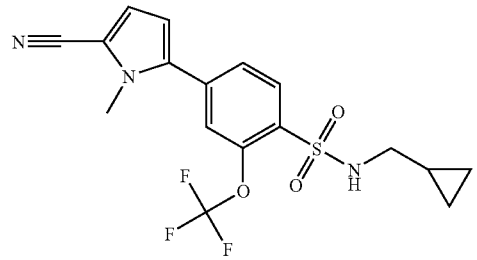

Step 1: According to general procedure C, 4-Bromo-2-trifluoromethoxy-benzenesulfonyl chloride (0.35 g, 1.03 mmol) and cyclopropylmethylamine (0.21 mL, 2.57 mmol) were stirred together with dry dichloromethane (5 mL) for 16 hours. 4-bromo-N-(cyclopropylmethyl)-2-(trifluoromethoxy)benzenesulfonamide (0.35 g, 91%) was provided after purification. MS (ESI) m/z 374. HPLC purity 100.0% at 210-370 nm, 9.9 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min Step 2: According to general procedure B, 4-bromo-N-(cyclopropylmethyl)-2-(trifluoromethoxy)benzenesulfonamide (224 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 µL, 0.02 mmol, 10 wt % in hexane) was added and the reaction was stirred for 16 hours. 4-(5-cyano-1-methyl-1H-pyrrol-2-yl)-N-(cyclopropylmethyl)-2-(trifluoromethoxy)benzenesulfonamide (56 mg, 24%) was provided after purification. MS (ESI) m/z 399. HPLC purity 99.1% at 210-370 nm, 9.9 min.; the Xterra® RP18 column, 3.5µ, 150×4.6 mm column, 1.2 mL/min., 85/15-5/95 (ammonium formate buffer pH=3.5/ACN+MeOH) for 10 min., hold 4 min.

Example 56

Preparation of 4-(5-cyano-1-methyl-1H-pyrrol-2-yl)-N-cyclobutyl-2-(trifluoromethoxy)benzenesulfonamide

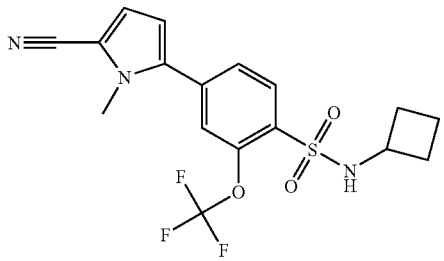

Step 1: According to general procedure C, 4-Bromo-2-trifluoromethoxy-benzenesulfonyl chloride (0.35 g, 1.03 mmol) and cyclobutylamine (0.21 mL, 2.57 mmol) were stirred together with dry dichloromethane (5 mL) for 16 hours. 4-bromo-N-cyclobutyl-2-(trifluoromethoxy)benzenesulfonamide (0.23 g, 61%) was provided after purification. MS (ESI) m/z 374. HPLC purity 100.0% at 210-370 nm, 10.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-cyclobutyl-2-(trifluoromethoxy)benzenesulfonamide (224 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium (0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-N-cyclobutyl-2-(trifluoromethoxy)benzenesulfonamide (56 mg, 24%) was provided after purification. MS (ESI) m/z 399. HPLC purity 99.4% at 210-370 nm, 10.0 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 57

Preparation of N-tert-butyl-4-(5-cyano-1-methyl-1H-pyrrol-2-yl)-2-(trifluoromethoxy)benzenesulfonamide

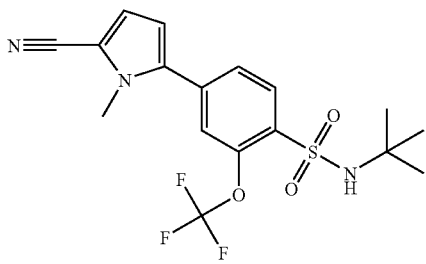

Step 1: According to general procedure C, 4-Bromo-2-trifluoromethoxy-benzenesulfonyl chloride (0.35 g, 1.03 mmol) and tert-butylamine (0.21 mL, 2.57 mmol) were stirred together with dry dichloromethane (5 mL) for 16 hours. 4-bromo-N-tert-butyl-2-(trifluoromethoxy)benzenesulfonamide (0.33 g, 85%) was provided after purification. MS (ESI) m/z 376. HPLC purity 100.0% at 210-370 nm, 10.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-N-tert-butyl-2-(trifluoromethoxy)benzenesulfonamide (225 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. N-tert-butyl-4-(5-cyano-1-methyl-1H-pyrrol-2-yl)-2-(trifluoromethoxy)benzenesulfonamide (44 mg, 19%) was provided after purification. MS (ESI) m/z 401. HPLC purity 99.0% at 210-370 nm, 10.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 58

4-(5-cyano-1-methyl-1H-pyrrol-2-yl)-2-(dimethylamino)-N,N-dimethylbenzenesulfonamide

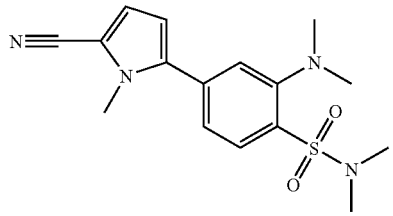

Step 1: According to general procedure A, 4-Bromo-2-fluoro-benzenesulfonyl chloride (0.40 g, 1.46 mmol) and dimethylamine (10 mL, 33% in ethanol) were stirred in a sealed tube for 16 hours. 4-bromo-2-(dimethylamino)-N,N-dimethylbenzenesulfonamide (0.19 g, 42%) was provided after purification. HRMS: calcd for $C_{10}H_{15}BrN_2O_2S+H^+$, 307.01103; found (ESI, [M+H]$^+$), 307.012. HPLC purity 100.0% at 210-370 nm, 9.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Step 2: According to general procedure B, 4-bromo-2-(dimethylamino)-N,N-dimethylbenzenesulfonamide (180 mg, 0.59 mmol), 5-cyano-1-methyl-1H-pyrrol-2-ylboronic acid (107 mg, 0.71 mmol), potassium fluoride (113 mg, 1.95 mmol), and tris(dibenzylideneacetone)dipalladium(0) (15 mg, 0.01 mmol) were placed in an oven dried flask under nitrogen and dry THF (1.4 mL) was added. Tri-t-butylphosphine (89 μL, 0.02 mmol, 10 wt % in hexane) was added and the reaction was stirred for 16 hours. 4-(5-cyano-1-methyl-1H-pyrrol-2-yl)-2-(dimethylamino)-N,N-dimethylbenzenesulfonamide (28 mg, 14%) was provided after purification. MS (ESI) m/z 332. HPLC purity 100.0% at 210-370 nm, 9.4 min.; the Xterra® RP18 column, 3.5μ, 150×4.6 mm column,

Example 59

Preparation of 4-(5-cyano-1-methyl-1H-pyrrol-2-yl)-2,5-difluoro-N-methylbenzenesulfonamide

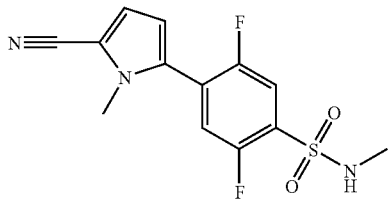

Step 1: According to general procedure C, 4-Bromo-2,5-difluorobenzenesulfonyl chloride (0.20 g, 0.68 mmol) and methylamine were stirred together in dichloromethane (1 mL) for 16 hours. The reaction afforded 4-bromo-2,5-difluoro-N-methylbenzenesulfonamide (0.17 g) after purification. HPLC purity 100.0% at 210-370 nm, 9.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_7H_6BrF_2NO_2S-H^+$, 283.91979; found (ESI-FTMS, $[M-H]^{1-}$), 283.92003

Step 2: According to general procedure B, 4-bromo-2,5-difluoro-N-methylbenzenesulfonamide (143 mg, 0.5 mmol), 5-cyano-1-methyl-1H-pyrrol-2-ylboronic acid (90 mg, 0.60 mmol), potassium fluoride (96 mg, 1.65 mmol), and tris(dibenzylideneacetone)dipalladium (12 mg, 0.013 mmol) were placed in an oven dried flask under nitrogen and dry THF (1.3 mL) was added. Tri-t-butylphosphine (75 μL, 0.026 mmol, 10 wt % in hexane) was added and the reaction was stirred for 16 hours. Purification afforded 4-(5-cyano-1-methyl-1H-pyrrol-2-yl)-2,5-difluoro-N-methylbenzenesulfonamide (24 mg). HPLC purity 87.6% at 210-370 nm, 8.4 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_{13}H_{11}F_2N_3O_2S-H^+$, 310.04673; found (ESI-FTMS, $[M-H]^{-1}$), 310.04692

Example 60

Preparation of 4-(5-cyano-1-methyl-1H-pyrrol-2-yl)-2,5-difluoro-N-isopropylbenzenesulfonamide

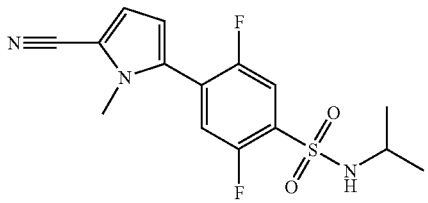

Step 1: According to general procedure C, 4-Bromo-2,5-difluorobenzenesulfonyl chloride (0.20 g, 0.68 mmol) and isopropylamine were stirred together in dichloromethane (1 mL) for 16 hours. The reaction afforded 4-bromo-2,5-difluoro-N-isopropylbenzenesulfonamide (0.16 g) after purification. HPLC purity 96.6% at 210-370 nm, 10.7 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_9H_{10}BrF_2NO_2S-H^+$, 311.95109; found (ESI-FTMS, $[M-H]^{1-}$), 311.95114

Step 2: According to general procedure B, 4-bromo-2,5-difluoro-N-isopropylbenzenesulfonamide (150 mg, 0.5 mmol), 5-cyano-1-methyl-1H-pyrrol-2-ylboronic acid (90 mg, 0.60 mmol), potassium fluoride (96 mg, 1.65 mmol), and tris(dibenzylideneacetone)dipalladium (12 mg, 0.013 mmol) were placed in an oven dried flask under nitrogen and dry THF (1.3 mL) was added. Tri-t-butylphosphine (75 μL, 0.026 mmol, 10 wt % in hexane) was added and the reaction was stirred for 16 hours. Purification afforded 4-(5-cyano-1-methyl-1H-pyrrol-2-yl)-2,5-difluoro-N-isopropylbenzenesulfonamide (24 mg) HPLC purity 97.2% at 210-370 nm, 9.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_{15}H_{15}F_2N_3O_2S-H^+$, 338.07803; found (ESI-FTMS, $[M-H]^{1-}$), 338.07811

Example 61

Preparation of 4-(5-cyano-1-methyl-1H-pyrrol-2-yl)-N-cyclopropyl-2,5-difluorobenzenesulfonamide

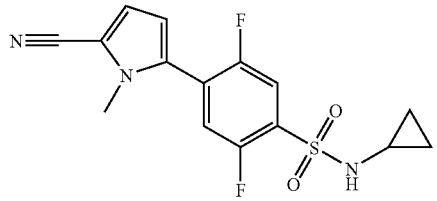

Step 1: According to general procedure C, 4-Bromo-2,5-difluorobenzenesulfonyl chloride (0.20 g, 0.68 mmol) and cyclopropylamine were stirred together in dichloromethane (1 mL) for 16 hours. The reaction afforded 4-bromo-N-cyclopropyl-2,5-difluorobenzenesulfonamide (0.17 g) after purification. HPLC purity 99.2% at 210-370 nm, 10.2 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_9H_8BrF_2NO_2S-H^+$, 309.93544; found (ESI-FTMS, $[M-H]^{1-}$), 309.93545

Step 2: According to general procedure B, 4-bromo-N-cyclopropyl-2,5-difluorobenzenesulfonamide (150 mg, 0.5 mmol), 5-cyano-1-methyl-1H-pyrrol-2-ylboronic acid (90 mg, 0.60 mmol), potassium fluoride (96 mg, 1.65 mmol), and tris(dibenzylideneacetone)dipalladium (12 mg, 0.013 mmol) were placed in an oven dried flask under nitrogen and dry THF (1.3 mL) was added. Tri-t-butylphosphine (75 μL, 0.026 mmol, 10 wt % in hexane) was added and the reaction was stirred for 16 hours. Purification afforded 4-(5-cyano-1-methyl-1H-pyrrol-2-yl)-N-cyclopropyl-2,5-difluorobenzenesulfonamide (33 mg) HPLC purity 99.0% at 210-370 nm, 9.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_{15}H_{13}F_2N_3O_2S-H^+$, 336.06238; found (ESI-FTMS, $[M-H]^{1-}$), 336.06247

Example 62

Preparation of 4-(5-cyano-1-methyl-1H-pyrrol-2-yl)-N-(cyclopropylmethyl)-2,5-difluorobenzenesulfonamide (WYE-100761)

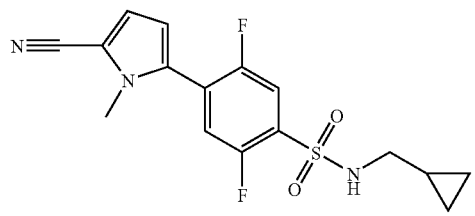

Step 1: According to general procedure C, 4-Bromo-2,5-difluorobenzenesulfonyl chloride (0.20 g, 0.68 mmol) and cyclopropylmethylamine were stirred together in dichloromethane (1 mL) for 16 hours. The reaction afforded 4-bromo-N-(cyclopropylmethyl)-2,5-difluorobenzenesulfonamide (0.17 g) after purification. HPLC purity 95.0% at 210-370 nm, 9.3 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_{10}H_{10}BrF_2NO_2S-H^+$, 323.95109; found (ESI-FTMS, $[M-H]^{1-}$), 323.95103

Step 2: According to general procedure B, 4-bromo-N-(cyclopropylmethyl)-2,5-difluorobenzenesulfonamide (150 mg, 0.5 mmol), 5-cyano-1-methyl-1H-pyrrol-2-ylboronic acid (90 mg, 0.60 mmol), potassium fluoride (96 mg, 1.65 mmol), and tris(dibenzylideneacetone)dipalladium (12 mg, 0.013 mmol) were placed in an oven dried flask under nitrogen and dry THF (1.3 mL) was added. Tri-t-butylphosphine (75 μL, 0.026 mmol, 10 wt % in hexane) was added and the reaction was stirred for 16 hours. Purification afforded 4-(5-cyano-1-methyl-1H-pyrrol-2-yl)-N-(cyclopropylmethyl)-2,5-difluorobenzenesulfonamide (47 mg). HPLC purity 98.2% at 210-370 nm, 9.5 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min. HRMS: calcd for $C_{16}H_{15}F_2N_3O_2S-H^+$, 350.07803; found (ESI-FTMS, $[M-H]^{1-}$), 350.07826

Example 63

Preparation of 4-(5-cyano-1-methyl-1H-pyrrol-2-yl)benzenesulfonamide

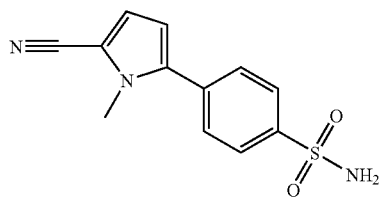

According to general procedure B, 4-bromobenzenesulfonamide (472 mg, 2.0 mmol), 5-cyano-1-methyl-1H-pyrrol-2-ylboronic acid (360 mg, 2.4 mmol), potassium fluoride (350 mg, 6.0 mmol), and tris(dibenzylideneacetone)-dipalladium (48 mg, 0.05 mmol) were placed in an oven dried flask under nitrogen and dry THF (5 mL) was added. Tri-t-butylphosphine (0.30 mL, 0.1 mmol, 10 wt % in hexane) was added and the reaction was stirred for 16 hours. Purification afforded 4-(5-cyano-1-methyl-1H-pyrrol-2-yl)benzenesulfonamide (190 mg). MS (ES) m/z 261.8; HPLC purity 99.6% at 210-370 nm, 7.1 min.; the Xterra® RP18 column, 3.5μ, 150×4.6 mm column, 1.2 mL/min., 85/15-5/95 (ammonium formate buffer pH=3.5/ACN+MeOH) for 10 min., hold 4 min.

Example 64

Effects of Progestins and Antiprogestins on Alkaline Phosphatase Activity in T47D Cells This example was performed to identify progestins or antiprogestins by determining a compound's effect on alkaline phosphatase activity in T47D cells.

Materials and Methods

A. Reagents:

Culture medium: DMEM:F12 (1:1) (GIBCO, BRL) supplemented with 5% (v/v) charcoal stripped fetal bovine serum (not heat-inactivated), 100 U/mL penicillin, 100 μg/mL streptomycin, and 2 mM the GlutaMax™ reagent (GIBCO, BRL).

Alkaline phosphatase assay buffer:
I. 0.1M Tris-HCl, pH 9.8, containing 0.2% the Triton® X-100 reagent
II. 0.1 M Tris-HCl, pH 9.8, containing 4 mM p-nitrophenyl phosphate (Sigma).

B. Cell Culture and Treatment:

Frozen T47D cells were thawed in a 37° C. water bath and diluted to 280,000 cells/mL in culture medium. To each well in a 96-well plate (Falcon, Becton Dickinson Labware), 180 μL of diluted cell suspension was added. Twenty μL of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hours. NOTE: For high throughput screening, one concentration of each compound was tested at 0.3 μg/mL. Based on an average molecular weight of 300 g/mol for the compounds in the library, the concentration was approximately 1 μM. Subsequently, active compounds were tested in dose response assays to determine $EC_{50}$ and $IC_{50}$.

C. Alkaline Phosphatase Enzyme Assay:

At the end of treatment, the medium was removed from the plate. Fifty μL of assay buffer I was added to each well. The plates were shaken in a titer plate shaker for 15 minutes. 150 μL of assay buffer II was then added to each well. Optical density measurements were taken at 5 minute intervals for 30 minutes at a test wavelength of 405 nM.

Analysis of Results—Analysis of Dose-Response Data

For reference and test compounds, a dose response curve was generated for dose (X-axis) vs. the rate of enzyme reaction (slope) (Y-axis). Square root-transformed data was used for analysis of variance and nonlinear dose response curve fitting for both agonist and antagonist modes. Huber weighting was used to down-weight the effects of outliners. $EC_{50}$ or $IC_{50}$ values were calculated from the retransformed values. JMP software (SAS Institute, Inc.) was used for both one-way analysis of variance and non-4 linear dose response analysis in both single dose and dose response studies.

REFERENCE COMPOUNDS

Progesterone and trimegestone are reference progestins known in the art and typically show an $EC_{50}$ of about 0.1 nM to about 2.0 nM. RU486 is a reference antiprogestin known in the art and typically shows an $IC_{50}$ of about 0.1 nM to about 2.0 nM.

| Example | Active Dose (nM) | $IC_{50}$ (nM) |
|---|---|---|
| 1 | | 13.9 |
| 2 | | 81.3 |
| 3 | | 11.4 |
| 4 | | 23.8 |
| 5 | | 27.5 |
| 6 | | 47.9 |
| 7 | | 66.1 |
| 8 | | 48.4 |
| 9 | 10000 | |
| 10 | | 146.5 |
| 11 | | 132.2 |
| 12 | | 189.1 |
| 13 | | 13.9 |
| 14 | | 6.6 |
| 15 | | 58.9 |
| 16 | | 40.8 |
| 17 | | 27.6 |
| 18 | | 48.1 |
| 19 | | 35.8 |
| 20 | | 81.9 |
| 21 | | |
| 22 | | 80.4 |
| 23 | | 77.1 |
| 24 | | 45.8 |
| 25 | | 17.3 |
| 26 | | 115.1 |
| 27 | | 38.2 |
| 28 | | 34.9 |
| 29 | | 17 |
| 30 | | 91 |
| 31 | | 8.5 |
| 32 | | 127.8 |
| 33 | | 13.1 |
| 34 | | 65.6 |
| 35 | | 26.8 |
| 36 | | 26.5 |
| 37 | | 150.7 |
| 38 | | 9.7 |
| 39 | | 40.4 |
| 40 | | 18.1 |
| 41 | | 62.2 |
| 42 | | 48.1 |
| 43 | 30 | |
| 44 | | 45.6 |
| 45 | | 99.4 |
| 46 | | 75.8 |
| 47 | | |
| 48 | | 62.7 |
| 49 | | 121.5 |
| 50 | | 101.1 |
| 51 | | 32.5 |
| 52 | | 8.4 |
| 53 | | 22.7 |
| 54 | | 71.7 |
| 55 | | 12.3 |
| 56 | 30 | |
| 57 | 30 | |
| 58 | | 25.9 |
| 59 | | 36.1 |
| 60 | | 49.3 |
| 61 | 30 | |
| 62 | | 163.8 |
| 63 | | 99.5 |

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of the structure:

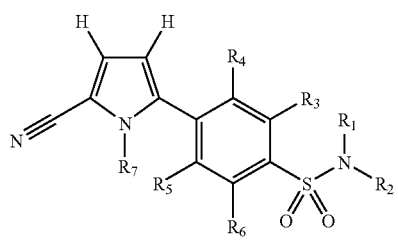

wherein:

$R_1$ and $R_2$ are independently selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heteroaryl, substituted heteroaryl, heterocycle, substituted heterocycle, $C_3$ to $C_6$ alkenyl, $C_3$ to $C_6$ substituted alkenyl, $C_3$ to $C_6$ alkynyl, substituted $C_3$ to $C_6$ alkynyl, —$(CH_mX_n)_zCH_pX_q$, O—$C_1$ to $C_6$ alkyl, O—$C_1$ to $C_6$ substituted alkyl, and O—$(CH_mX_n)_zCH_pX_q$; or $R_1$ and $R_2$ may be taken together to form a ring of 4 to 8 ring atoms containing in its backbone carbon atoms and 1 to 4 N, O, S, or $SO_2$, and where any C-atom or N-atom of said ring is optionally substituted with $C_1$ to $C_4$ alkyl, F, or $CF_3$;

$R_3$, $R_4$, $R_5$ and $R_6$ are independently selected from the group consisting of H, halogen, CN, $C_1$ to $C_6$ alkyl, substituted $C_1$ to $C_6$ alkyl, —$(CH_mX_n)_zCH_pX_q$, $C_3$ to $C_6$ cycloalkyl, substituted $C_3$ to $C_6$ cycloalkyl, O—$C_1$ to $C_6$ alkyl, O—$C_1$ to $C_6$ substituted alkyl, OH, $NH_2$, NH—$(CH_mX_n)_zCH_pX_q$, O—$(CH_mX_n)_zCH_pX_q$, N—$\{(CH_mX_n)_zCH_pX_q\}_2$, aryl, substituted aryl, heteroaryl, substituted heteroaryl, heterocycle, and substituted heterocycle;

X is halogen;

m and n are, independently, 0 to 2, provided that m+n=2;

p and q are, independently, 0 to 3, provided that p+q=3;

z is 0 to 10;

$R_7$ is selected from the group consisting of H, $C_1$ to $C_6$ alkyl, substituted $C_1$ to $C_6$ alkyl, $C_3$ to $C_6$ cycloalkyl, and substituted $C_3$ to $C_6$ cycloalkyl;

or a pharmaceutically acceptable salt or tautomer thereof.

2. The compound according to claim 1, wherein $R_7$ is a branched $C_3$ to $C_6$ alkyl.

3. The compound according to claim 1, wherein $R_3$, $R_4$, $R_5$, and $R_6$ are H.

4. The compound according to claim 1, wherein $R_4$ is H or halogen.

5. The compound according to claim 1, wherein $R_7$ is $C_1$ to $C_6$ alkyl.

6. The compound according to claim 1, wherein $R_1$ is H or $C_1$ to $C_6$ alkyl.

7. The compound according to claim 1, wherein $R_2$ is H, $C_1$ to $C_6$ alkyl, substituted $C_1$ to $C_6$ alkyl, $C_3$ to $C_6$ cycloalkyl, $CF_3$, or $CH_2$—$C_3$ to $C_8$ cycloalkyl.

8. The compound according to claim 1, wherein $R_1$ and $R_2$ are joined to form tetrahydropyrrole, pyrrolidine, piperidine, tetrahydropyran, or pyrrole.

9. The compound according to claim 1, wherein $R_3$ is H or $OCF_3$.

10. The compound according to claim 1, wherein $R_4$ and $R_6$ are independently H or F.

11. The compound according to claim 1, wherein $R_5$ is H, $CF_3$, $N(CH_3)_2$, or F.

12. The compound according to claim 1, wherein:

$R_1$ is H or $C_1$ to $C_6$ alkyl;

$R_2$ is H, $C_1$ to $C_6$ alkyl, substituted $C_1$ to $C_6$ alkyl, $C_3$ to $C_6$ cycloalkyl, or $CF_3$; or $R_1$ and $R_2$ are joined with the N-atom to form tetrahydropyrrole, piperidine, tetrahydropyran, or pyrrole;

$R_3$ is H or $OCF_3$;

$R_4$ and $R_6$ are independently H or F;

$R_5$ is H, $CF_3$, $N(CH_3)_2$, or F; or $R_7$ is $C_1$ to $C_6$alkyl.

13. The compound according to claim 1 which is selected from the group consisting of 4-(5-cyano-1-methyl-1H-pyrrol-2-yl)-N-methylbenzenesulfonamide; 4-(5-cyano-1-methyl-1H-pyrrol-2-yl)-N,N-dimethylbenzenesulfonamide; 4-(5-cyano-1-methyl-1H-pyrrol-2-yl)-N-ethylbenzenesulfonamide; 4-(5-cyano-1-methyl-1H-pyrrol-2-yl)-N-propylbenzenesulfonamide; 4-(5-cyano-1-methyl-1H-pyrrol-2-yl)-N-isopropylbenzenesulfonamide; 4-(5-cyano-1-methyl-1H-pyrrol-2-yl)-N-isobutylbenzenesulfonamide; 4-(5-cyano-1-methyl-1H-pyrrol-2-yl)-N-ethyl-N-methylbenzenesulfonamide; 4-(5-cyano-1-methyl-1H-pyrrol-2-yl)-N,N-diethylbenzenesulfonamide; N-(tert-butyl)-4-(5-cyano-1-methyl-1H-pyrrol-2-yl)benzenesulfonamide; 1-methyl-5-[4-(pyrrolidin-1-ylsulfonyl)phenyl]-1H-pyrrole-2-carbonitrile; 1-methyl-5-[4-(piperidin-1-ylsulfonyl)phenyl]-1H-pyrrole-2-carbonitrile; 1-methyl-5-[4-(morpholin-4-ylsulfonyl)phenyl]-1H-pyrrole-2-carbonitrile; 4-(5-cyano-1-methyl-1H-pyrrol-2-yl)-N-cyclobutylbenzenesulfonamide; 4-(5-cyano-1-methyl-1H-pyrrol-2-yl)-N-cyclopropylbenzenesulfonamide; 4-(5-cyano-1-methyl-1H-pyrrol-2-yl)-N-cyclohexylbenzenesulfonamide; 4-(5-cyano-1-methyl-1H-pyrrol-2-yl)-N-(2,2,2-trifluoroethyl)benzenesulfonamide; 4-(5-cyano-1-methyl-1H-pyrrol-2-yl)-N-(cyclopropylmethyl)benzenesulfonamide; 1-methyl-5-[4-(1H-pyrrol-1-ylsulfonyl)phenyl]-1H-pyrrole-2-carbonitrile; 4-(5-cyano-1-methyl-1H-pyrrol-2-yl)-2-(trifluoromethyl)benzenesulfonamide; 4-(5-cyano-1-methyl-1H-pyrrol-2-yl)-N,N-dimethyl-2-(trifluoromethyl)benzenesulfonamide; 4-(5-cyano-1-methyl-1H-pyrrol-2-yl)-N-methyl-2-(trifluoromethyl)benzenesulfonamide; 4-(5-cyano-1-methyl-1H-pyrrol-2-yl)-N,N-diethyl-2-(trifluoromethyl)benzenesulfonamide; 4-(5-cyano-1-methyl-1H-pyrrol-2-yl)-N-isopropyl-2(trifluoromethyl)benzenesulfonamide; 4-(5-cyano-1-methyl-1H-pyrrol-2-yl)-N-ethyl-2-(trifluoromethyl)benzenesulfonamide; 4-(5-cyano-1-methyl-1H-pyrrol-2-yl)-N-propyl-2-(trifluoromethyl)benzenesulfonamide; 1-methyl-5-[4-(pyrrolidin-1-ylsulfonyl)-3-(trifluoromethyl)phenyl]-1H-pyrrole-2-carbonitrile; 4-(5-cyano-1-methyl-1H-pyrrol-2-yl)-N-cyclopropyl-2-(trifluoromethyl)benzenesulfonamide; 4-(5-cyano-1-methyl-1H-pyrrol-2-yl)-N-(cyclopropylmethyl)-2-(trifluoromethyl)benzenesulfonamide; 4-(5-cyano-1-methyl-1H-pyrrol-2-yl)-N-cyclobutyl-2-(trifluoromethyl)benzenesulfonamide; 4-(5-cyano-1-methyl-1H-pyrrol-2-yl)-3-fluorobenzenesulfonamide; 4-(5-cyano-1-methyl-1H-pyrrol-2-yl)-3-fluoro-N-methylbenzenesulfonamide; 4-(5-cyano-1-methyl-1H-pyrrol-2-yl)-3-fluoro-N,N-dimethylbenzenesulfonamide; 4-(5-cyano-1-methyl-1H-pyrrol-2-yl)-N-ethyl-3-fluorobenzenesulfonamide; 4-(5-cyano-1-methyl-1H-pyrrol-2-yl)-N,N-diethyl-3-fluorobenzenesulfonamide; 4-(5-cyano-1-methyl-1H-pyrrol-2-yl)-3-fluoro-N-isopropylbenzenesulfonamide; 4-(5-cyano-1-methyl-1H-pyrrol-2-yl)-3-fluoro-N-propylbenzenesulfonamide; 5-[2-fluoro-4-(pyrrolidin-1-ylsulfonyl)phenyl]-1-methyl-1H-pyrrole-2-carbonitrile; 4-(5-cyano-1-methyl-1H-pyrrol-2-yl)-N-cyclopropyl-3-fluorobenzenesulfonamide; 4-(5-cyano-1-methyl-1H-pyrrol-2-yl)-N-(cyclopropylmethyl)-3-fluorobenzenesulfonamide; 4-(5-cyano-1-methyl-1H-pyrrol-2-yl)-N-cyclobutyl-3-fluorobenzenesulfonamide; 4-(5-cyano-1-methyl-1H-pyrrol-2-yl)-N,N-diethyl-2-fluorobenzenesulfonamide; 4-(5-cyano-1-methyl-1H-pyrrol-2-yl)-2-fluoro-N-isopropylbenzenesulfonamide; 4-(5-cyano-1-methyl-1H-pyrrol-2-yl)-N-cyclopropyl-2-fluorobenzenesulfonamide; 4-(5-cyano-1-methyl-1H-pyrrol-2-yl)-N-(cyclopropylmethyl)-2-fluorobenzenesulfonamide; 4-(5-cyano-1-methyl-1H-pyrrol-2-yl)-N-cyclobutyl-2-fluorobenzenesulfonamide; 4-(5-cyano-1-methyl-1H-pyrrol-2-yl)-2-(trifluoromethoxy)benzenesulfonamide; 4-(5-cyano-1-methyl-1H-pyrrol-2-yl)-N-methyl-2-(trifluoromethoxy)benzenesulfonamide; 4-(5-cyano-1-methyl-1H-pyrrol-2-yl)-N,N-dimethyl-2-(trifluoromethoxy)benzenesulfonamide; 4-(5-cyano-1-methyl-1H-pyrrol-2-yl)-N-ethyl-2-(trifluoromethoxy)benzenesulfonamide; 4-(5-cyano-1-methyl-1H-pyrrol-2-yl)-N,N-diethyl-2-(trifluoromethoxy)benzenesulfonamide; 4-(5-cyano-1-methyl-1H-pyrrol-2-yl)-N-isopropyl-2-(trifluoromethoxy)benzenesulfonamide; 4-(5-cyano-1-methyl-1H-pyrrol-2-yl)-N-propyl-2-(trifluoromethoxy)benzenesulfonamide; 1-methyl-5-[4-(pyrrolidin-1-ylsulfonyl)-3-(trifluoromethoxy)phenyl]-1H-pyrrole-2-carbonitrile; 4-(5-cyano-1-methyl-1H-pyrrol-2-yl)-N-cyclopropyl-2-(trifluoromethoxy)benzenesulfonamide; 4-(5-cyano-1-methyl-1H-pyrrol-2-yl)-N-(cyclopropylmethyl)-2-(trifluoromethoxy)benzenesulfonamide; 4-(5-cyano-1-methyl-1H-pyrrol-2-yl)-N-cyclobutyl-2-(trifluoromethoxy)benzenesulfonamide; N-tert-butyl-4-(5-cyano-1-methyl-1H-pyrrol-2-yl)-2-(trifluoromethoxy)benzenesulfonamide; 4-(5-cyano-1-methyl-1H-pyrrol-2-yl)-2-(dimethylamino)-N,N-dimethylbenzenesulfonamide; 4-(5-cyano-1-methyl-1H-pyrrol-2-yl)-2,5-difluoro-N-methylbenzenesulfonamide; 4-(5-cyano-1-methyl-1H-pyrrol-2-yl)-2,5-difluoro-N-isopropylbenzenesulfonamide; 4-(5-cyano-1-methyl-1H-pyrrol-2-yl)-N-cyclopropyl-2,5-difluorobenzenesulfonamide; 4-(5-cyano-1-methyl-1H-pyrrol1-2-yl)-N-(cyclopropylmethyl)-2,5-difluorobenzenesulfonamide; and a pharmaceutically acceptable salt or tautomer thereof.

* * * * *